United States Patent
Weber

(10) Patent No.: US 8,603,045 B2
(45) Date of Patent: Dec. 10, 2013

(54) INJECTION DEVICE

(75) Inventor: Wilfried Weber, Schopfloch (DE)

(73) Assignee: Bayer Intellectual Property GmbH, Monheim (DE)

( * ) Notice: Subject to any disclaimer, the term of this patent is extended or adjusted under 35 U.S.C. 154(b) by 778 days.

(21) Appl. No.: 12/663,585

(22) PCT Filed: Jun. 3, 2008

(86) PCT No.: PCT/EP2008/004412
§ 371 (c)(1),
(2), (4) Date: Jan. 15, 2010

(87) PCT Pub. No.: WO2008/148518
PCT Pub. Date: Dec. 11, 2008

(65) Prior Publication Data
US 2011/0028910 A1 Feb. 3, 2011

(30) Foreign Application Priority Data

Jun. 8, 2007 (DE) .................... 20 2007 008 068 U
Sep. 8, 2007 (DE) .................... 20 2007 012 637 U

(51) Int. Cl.
*A61M 5/315* (2006.01)

(52) U.S. Cl.
USPC ........................ 604/218; 604/131; 604/232

(58) Field of Classification Search
USPC .......... 604/82, 117, 131, 134–137, 151, 152, 604/156, 157, 208–211, 218, 224, 232
See application file for complete search history.

(56) References Cited

U.S. PATENT DOCUMENTS

| 6,270,479 | B1 | 8/2001 | Bergens et al. |
| 6,454,743 | B1 * | 9/2002 | Weber ........................ 604/131 |
| 2002/0183690 | A1 * | 12/2002 | Arnisolle ...................... 604/83 |
| 2005/0273055 | A1 | 12/2005 | Harrison |
| 2006/0258990 | A1 | 11/2006 | Weber |
| 2008/0188798 | A1 | 8/2008 | Weber |

FOREIGN PATENT DOCUMENTS

| WO | 2004054645 A2 | 7/2004 |
| WO | 2005011780 A2 | 2/2005 |
| WO | 2007033638 A1 | 3/2007 |

* cited by examiner

*Primary Examiner* — Kami A Bosworth
(74) *Attorney, Agent, or Firm* — Browdy and Neimark, PLLC

(57) ABSTRACT

An injection device having parts, the relative movement of which causes the active substance to be injected. For this purpose, a receptacle, into and in which a carpule/syringe can be inserted and mounted, is retained in a housing, the receptacle can be moved by means of a carriage, and a plunger that applies a force to the piston/s of the carpule/syringe is movably retained in the receptacle. A traction rope which is deflected by means of a roll mounted on the carriage is provided for performing the pricking stroke, injection stroke, and retracting stroke. One end of the traction rope is connected to the receptacle while the other end thereof is connected to a tension spring that is retained on the housing. Mechanisms between the housing, the receptacle, the plunger, and the carriage control the reciprocal coupling thereof to the traction rope.

12 Claims, 23 Drawing Sheets

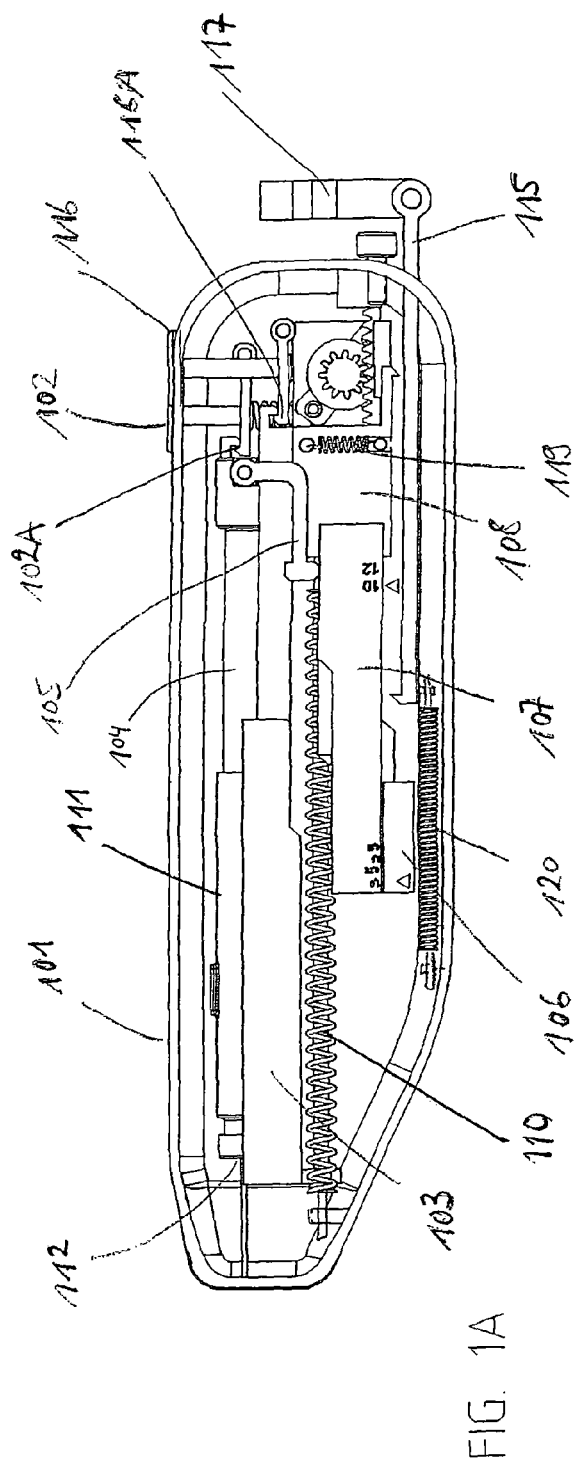
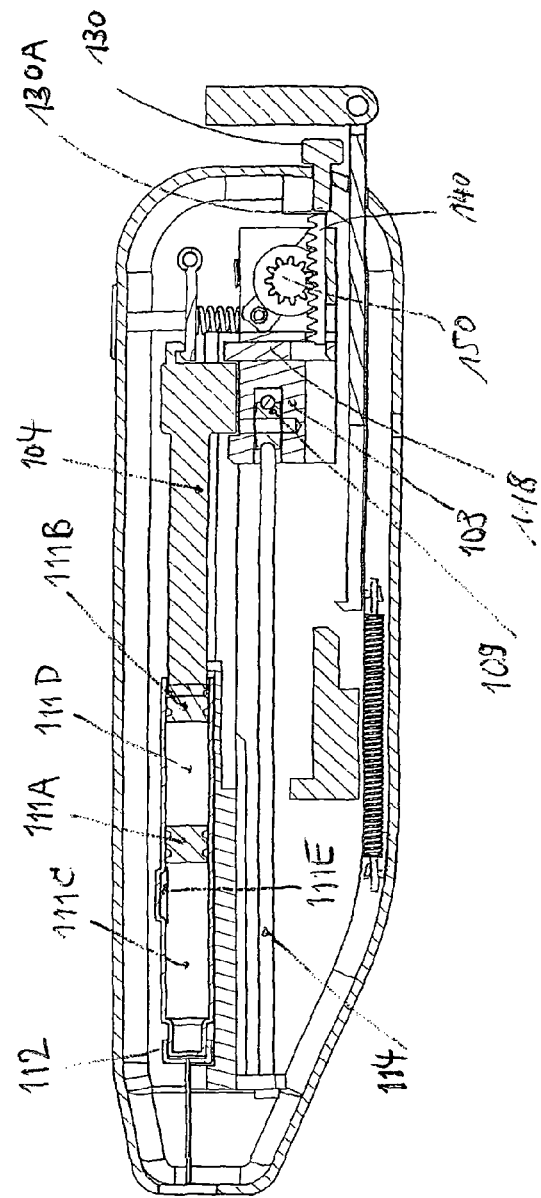
FIG. 1A
FIG. 1B

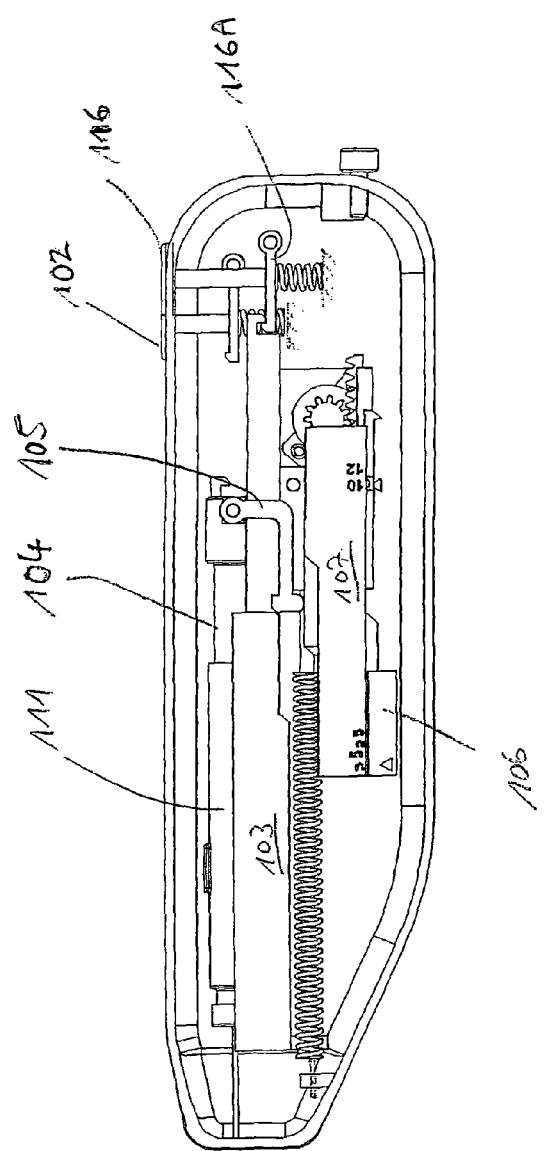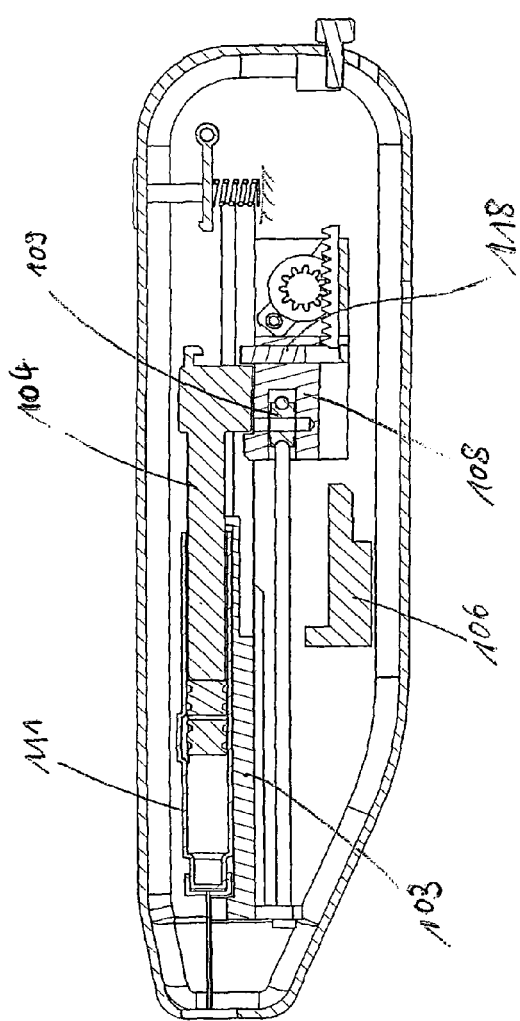
FIG. 2A
FIG. 2B

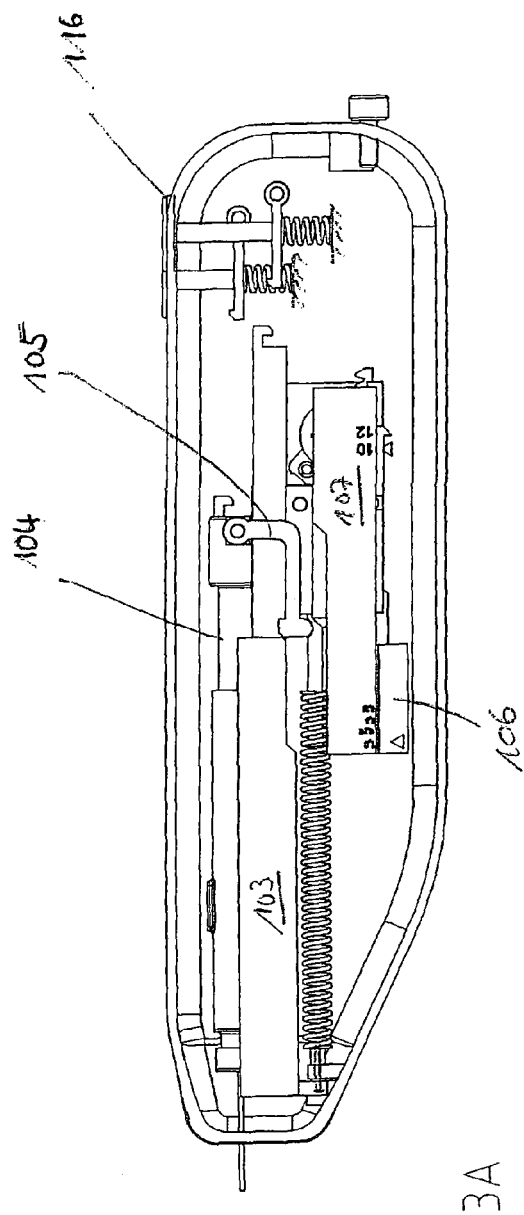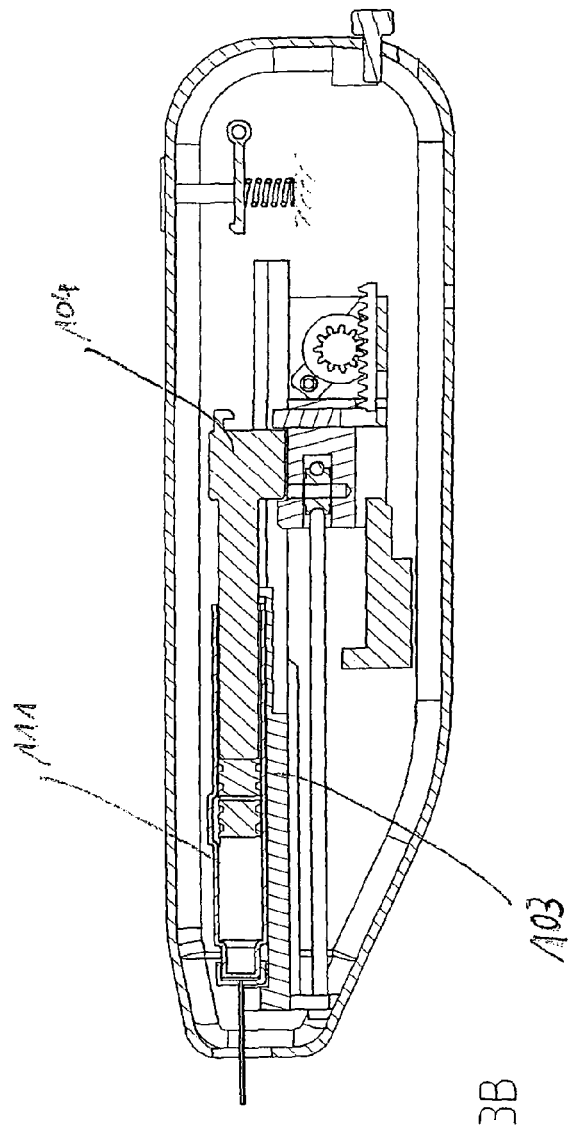

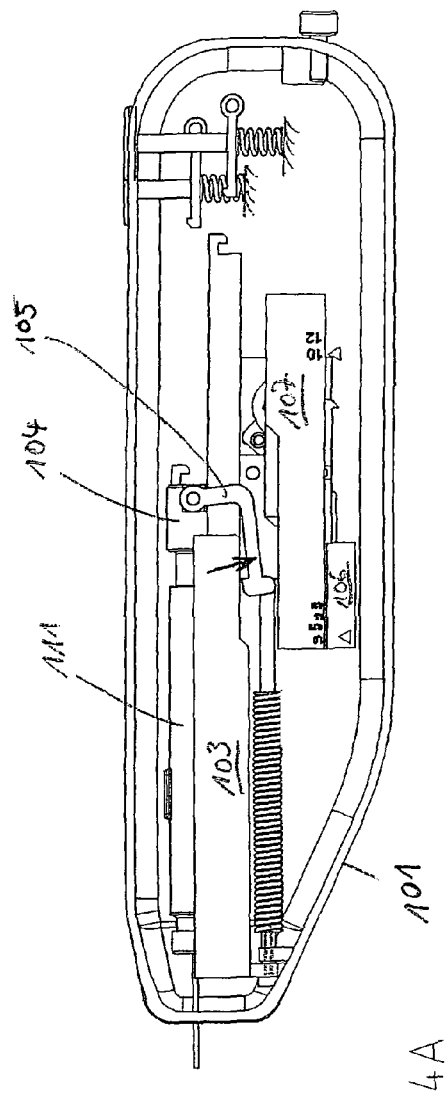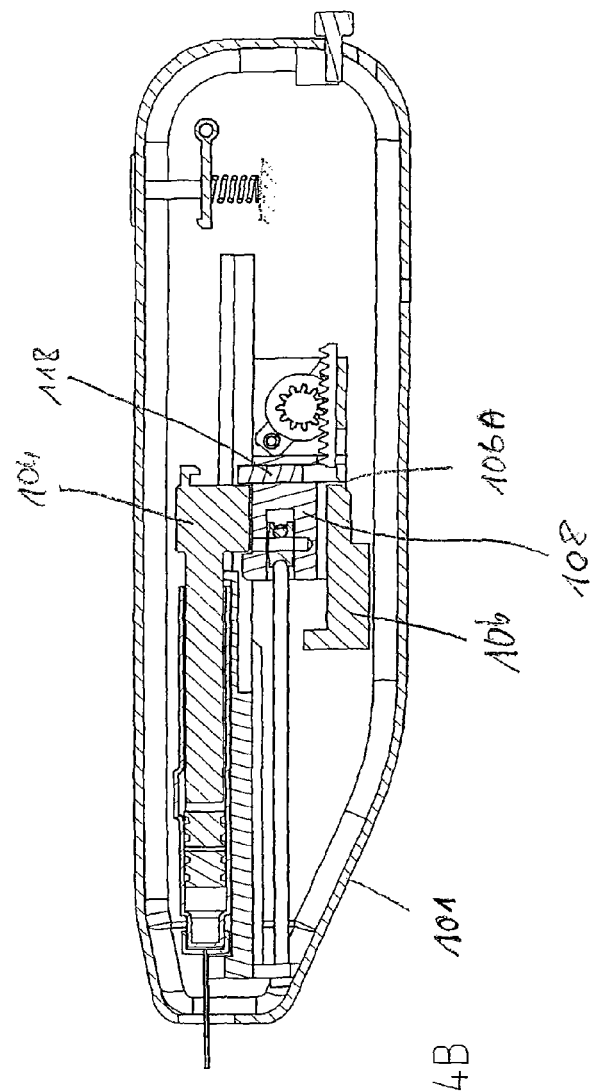
FIG. 4A
FIG. 4B

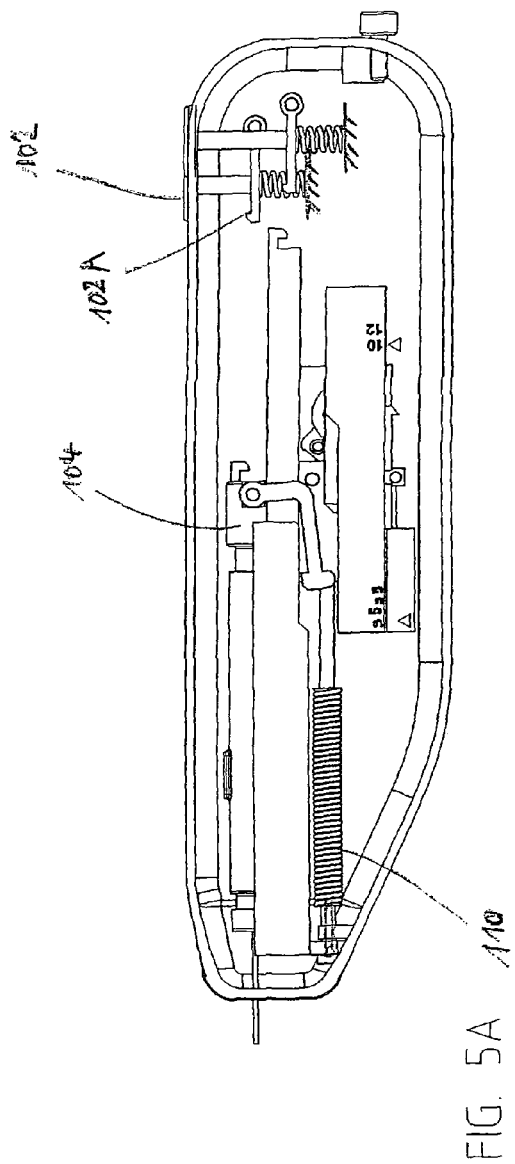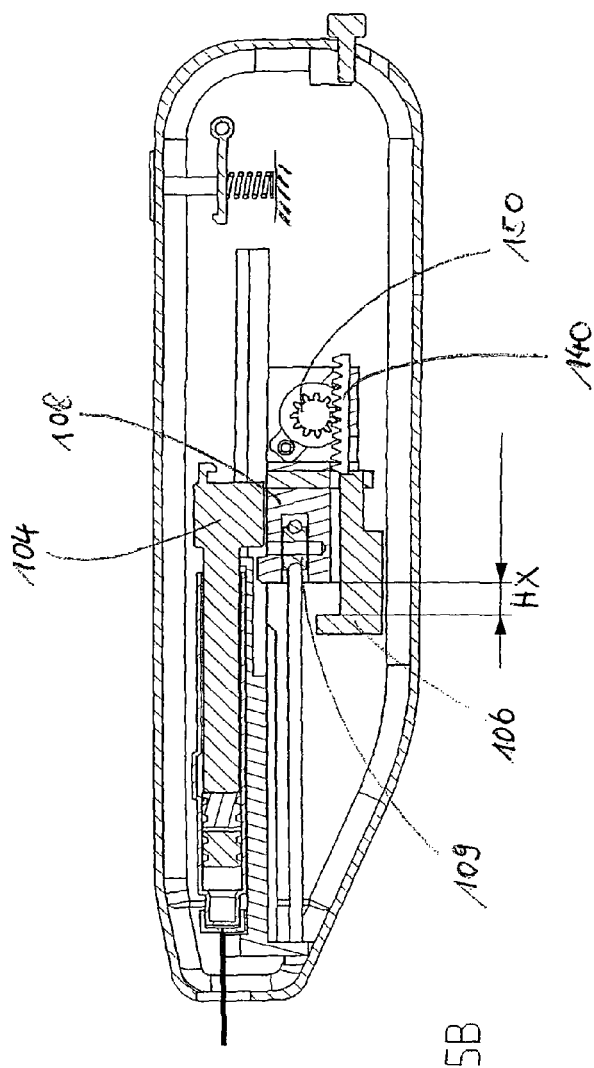
FIG. 5A
FIG. 5B

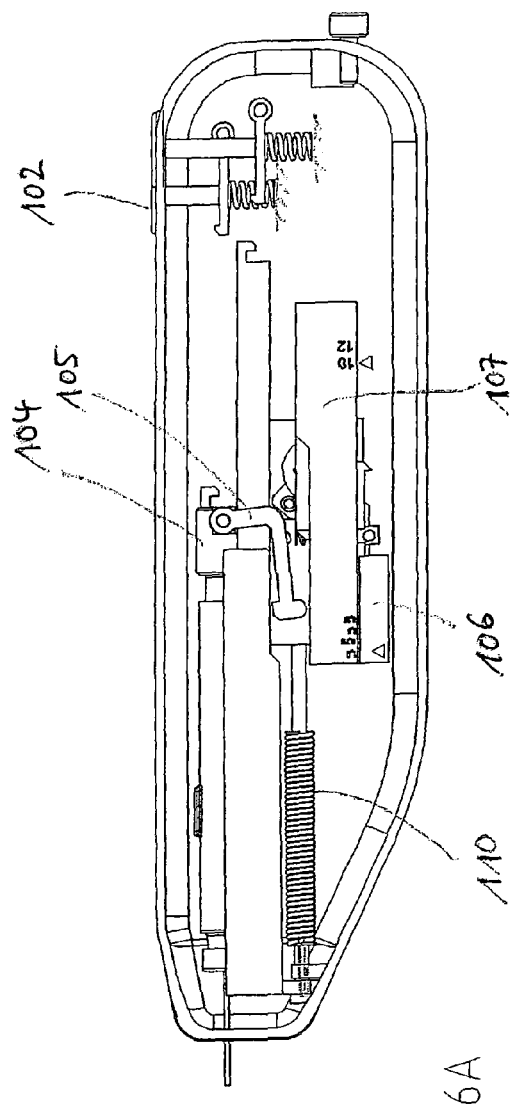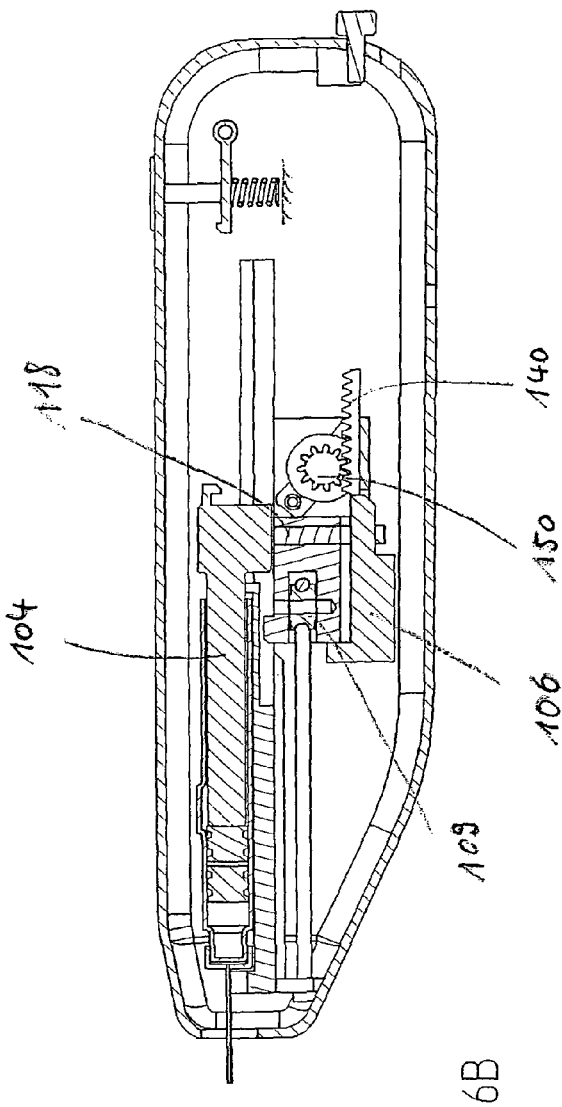
FIG. 6A
FIG. 6B

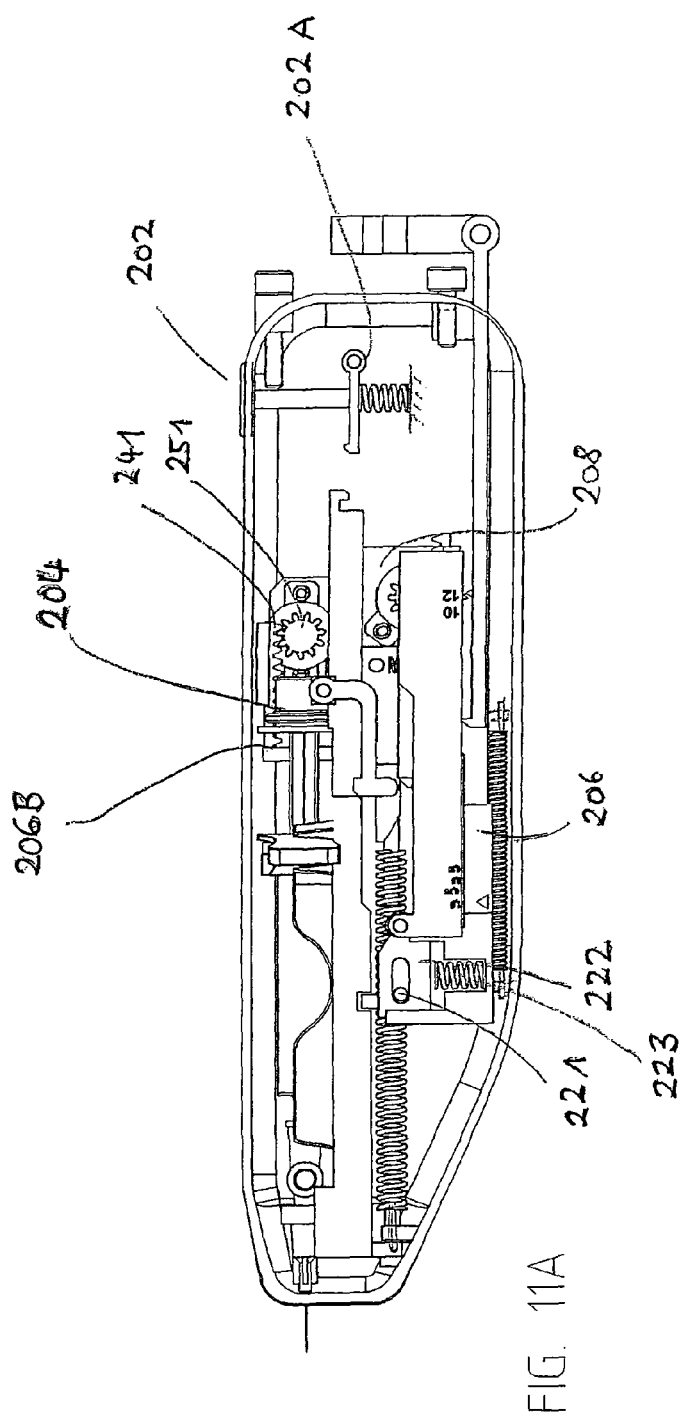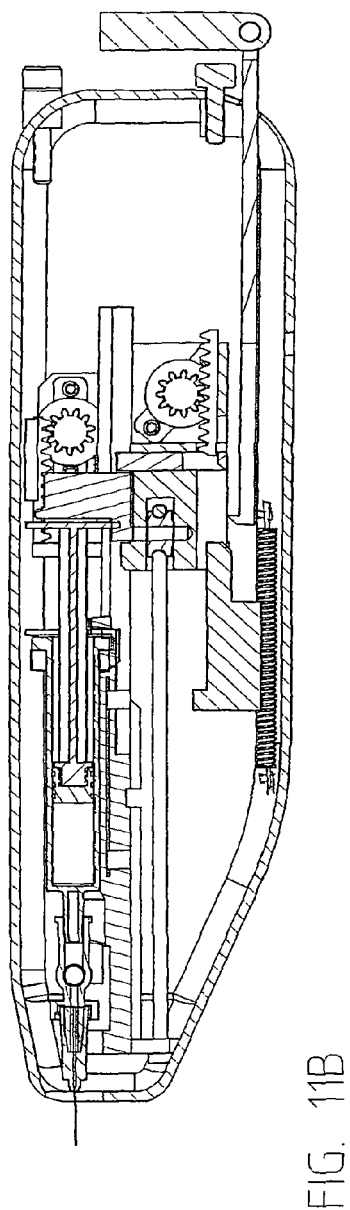
FIG. 11A
FIG. 11B

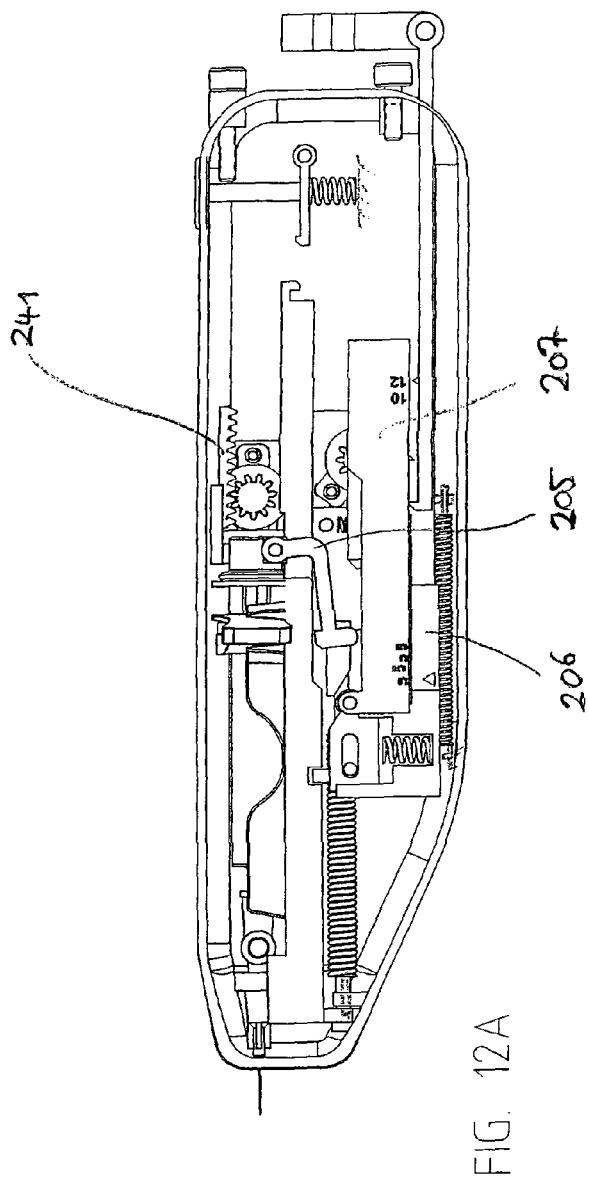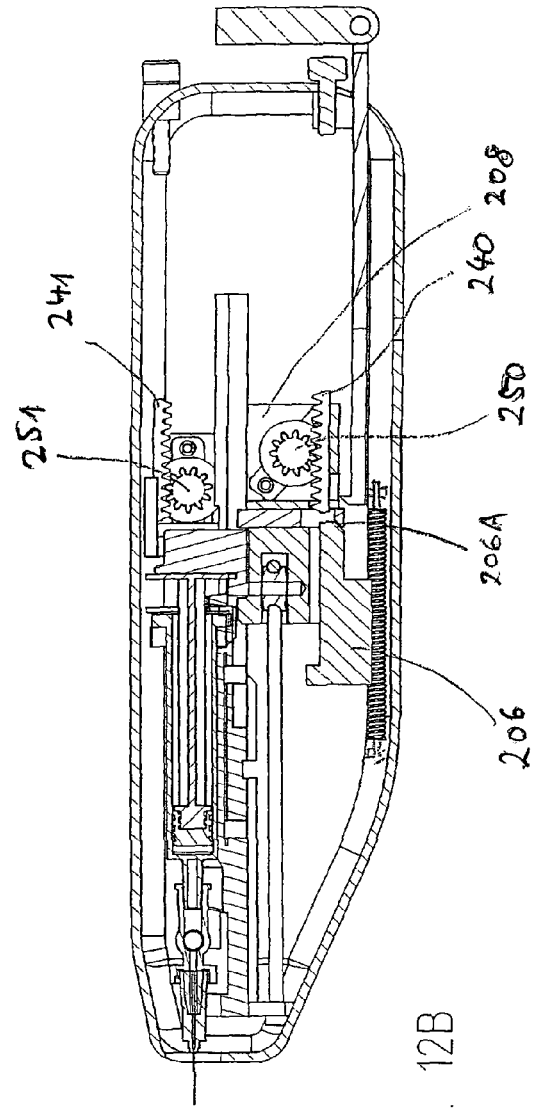

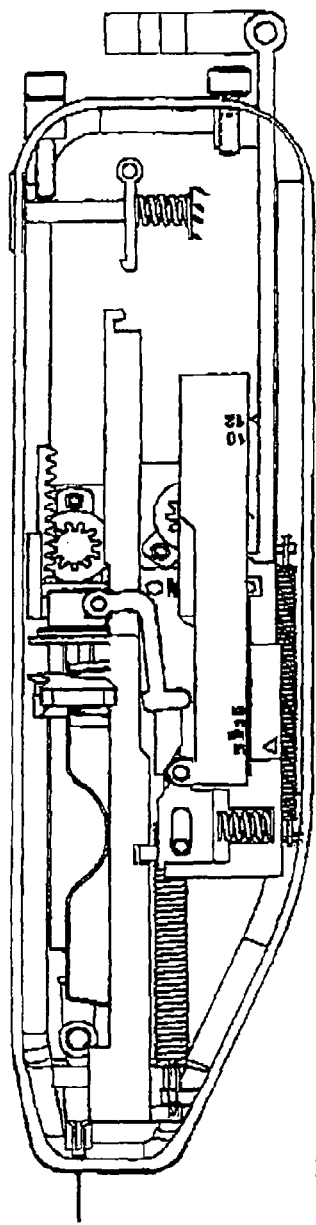
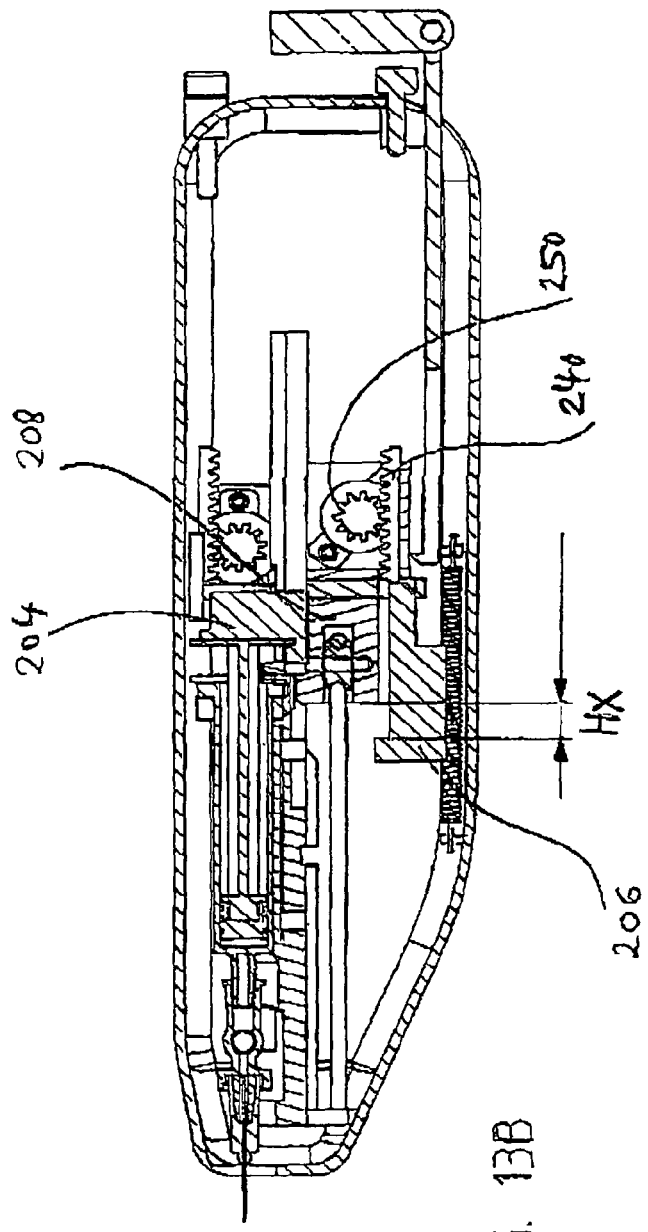
FIG. 13A
FIG. 13B

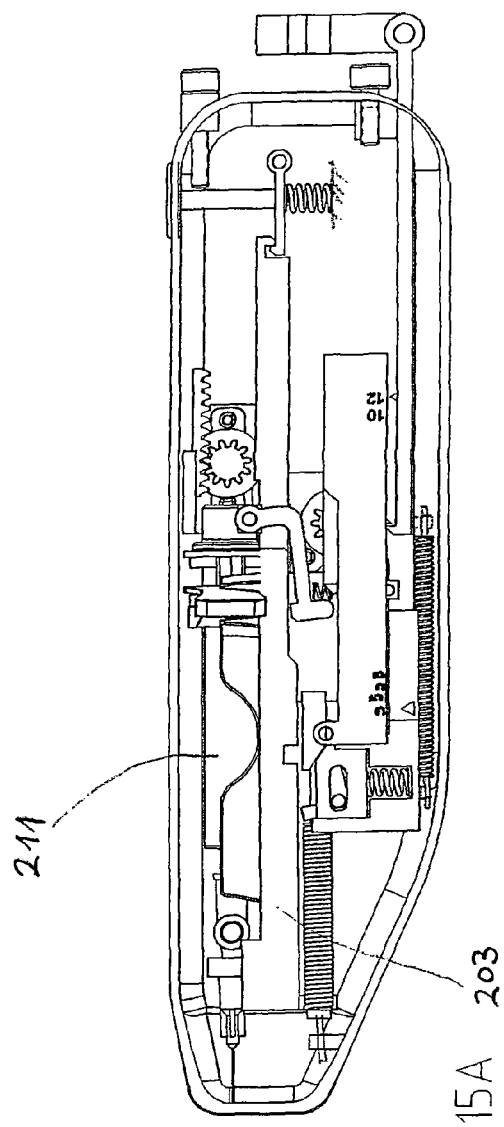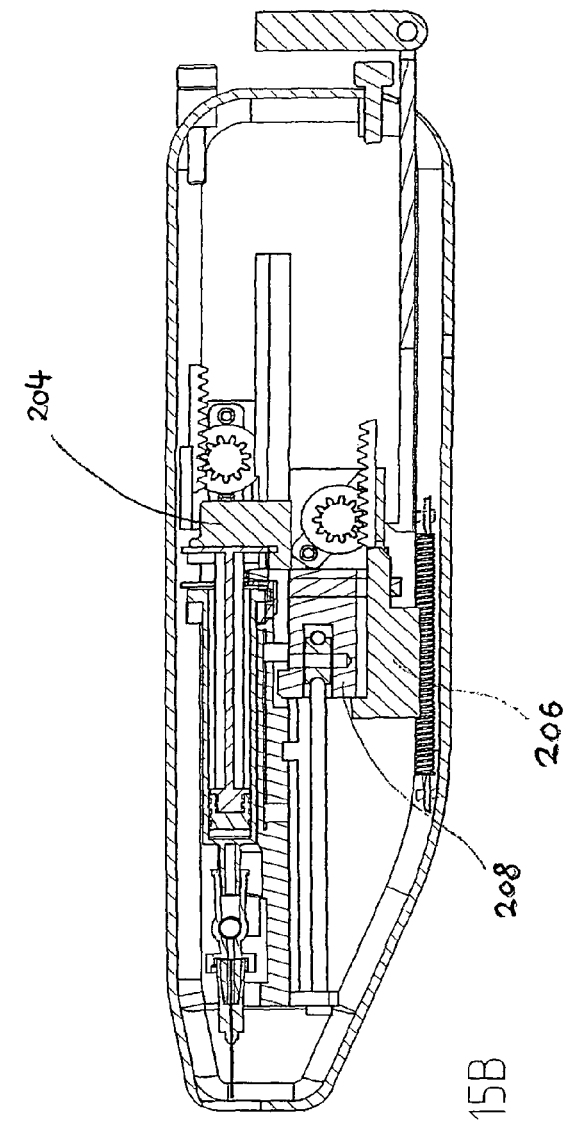
FIG. 15A
FIG. 15B

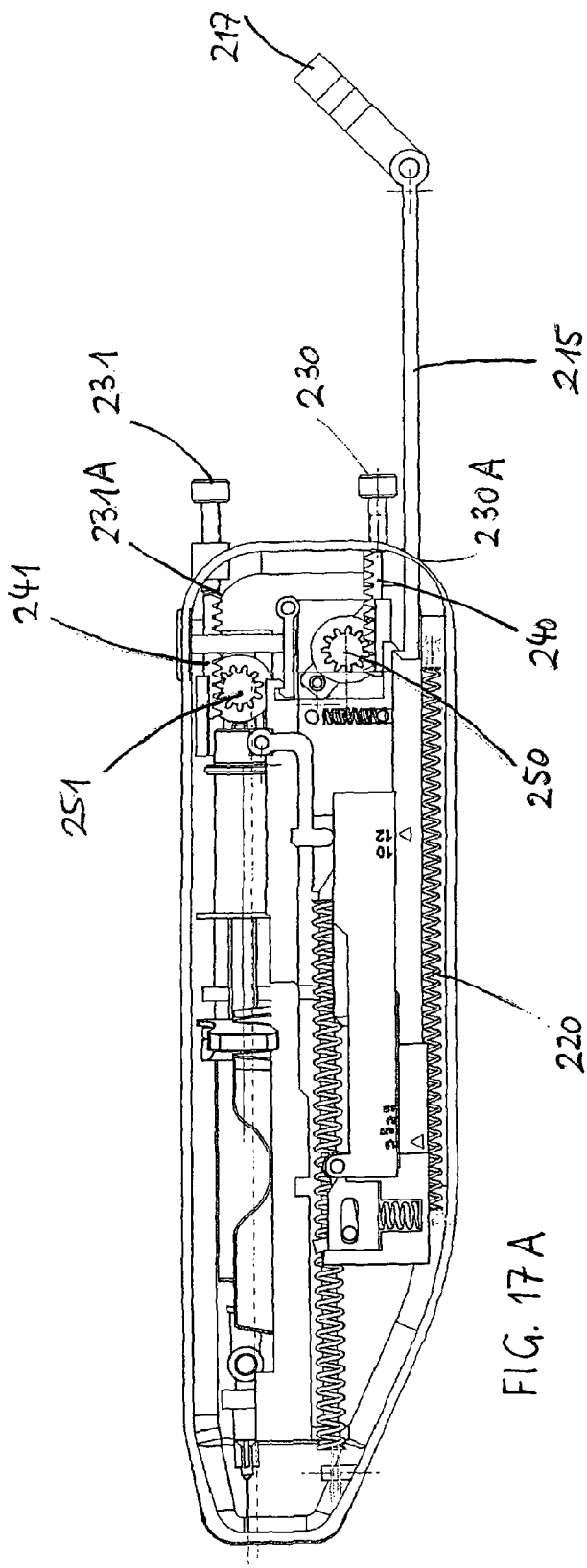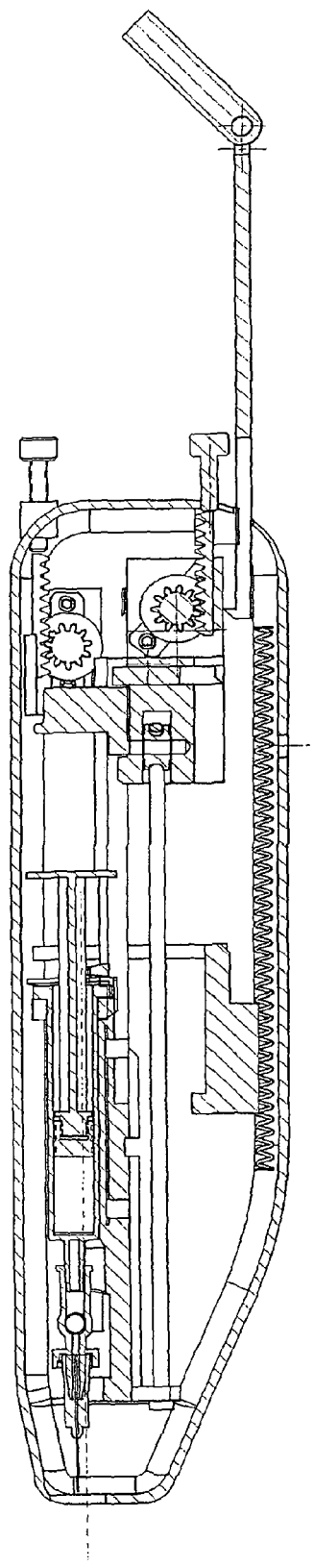
FIG. 17A
FIG. 17B

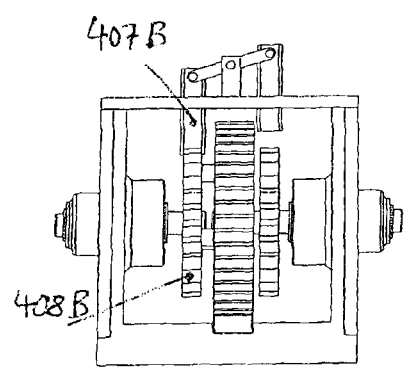
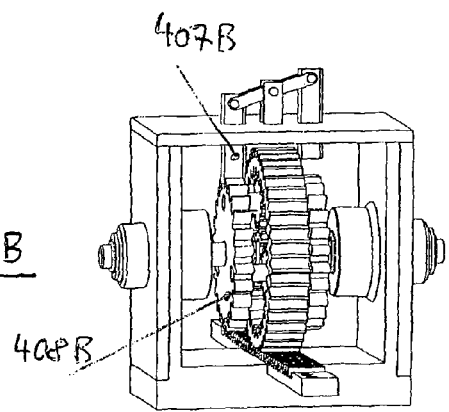
FIG. 19B
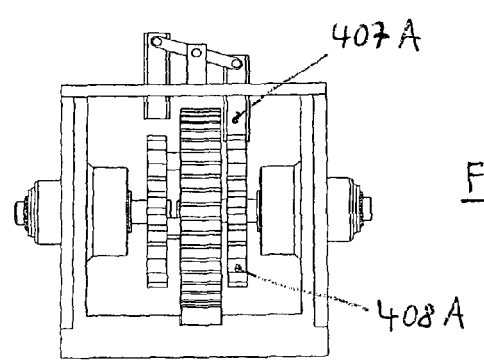
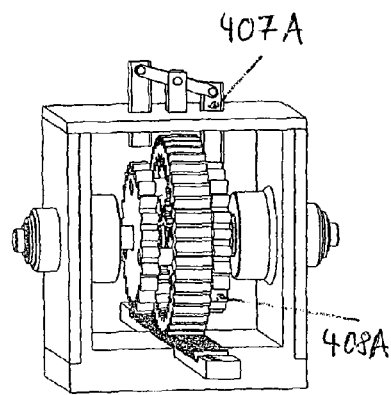
FIG. 19C

INJECTION DEVICE

TECHNICAL BACKGROUND

For the treatment of a multitude of illnesses, which are now widespread, such as diabetes, patients must inject themselves independently with the needed amount of an active substance/medicament, using a hypodermic syringe or a carpule. To make this safer and easier, a multitude of injection devices are known that incorporate a largely automatic sequence of insertion of the needle, injection of the active substance and withdrawal of the needle.

PRIOR ART

For the use of disposable hypodermic syringes, a number of devices for automatic injection of the active substance that is contained in the syringe are known; document WO 2007/033638, for instance, which forms the prior art, discloses an injection device which, while simple to operate, permits a fully automatic sequence of the above-described processes, using a two-chamber ampoule whereby a sequence of mixing, needle-insertion and injection is made possible.

DISCLOSURE OF THE INVENTION

It is the object of the invention to improve an injection device in such a way that the handling comfort and safety for the patient is improved, while providing for a simple mechanical design.

The inventive injection device meets this object with the characteristics of claim 1.

It is the underlying idea of the invention that the previously seamless progression of the strokes with a fixed stroke duration in each case is now no longer predefined, but the user is instead enabled to individually design the duration of the stroke (and, hence, the speed of the respective associated process, such as e.g. the injection), as well as the transition of individual strokes (and thereby in particular pauses in the sequence of the movements.)

Preferred embodiments relate to the design of the component parts for adjusting the retention time and injection duration.

BRIEF DESCRIPTION OF THE DRAWINGS

Two preferred exemplary embodiments of the injection device will now be explained with the aid of drawings, in which FIG. 1A shows a side view of a first exemplary embodiment of the injection device with the housing cover removed, FIG. 1B shows a section through the injection device of FIG. 1 in its starting position in its center plane, FIG. 2A shows a side view of the injection device in the process of carrying out the mixing stroke, FIG. 2B shows a sectional view corresponding to FIG. 2A, FIG. 3A shows a side view of the injection device during the puncture stroke, FIG. 3B shows a sectional view according to FIG. 3A, FIG. 4A shows a side view of the injection device during the injection stroke, FIG. 4B shows a sectional view corresponding to FIG. 4A, FIG. 5A shows a side view of a first exemplary embodiment of the injection device during the idle stroke, FIG. 5B shows a sectional view corresponding to FIG. 5A, FIG. 6A shows a side view of a first exemplary embodiment of the injection device during withdrawal of the needle, and FIG. 6B shows a sectional view corresponding to FIG. 6A, FIG. 11A shows a side view of a second exemplary embodiment of the injection device during the puncture stroke, FIG. 11B shows a sectional view corresponding to FIG. 11A, FIG. 12A shows a side view of a second exemplary embodiment of the injection device during the injection stroke, FIG. 12B shows a sectional view corresponding to FIG. 12A, FIG. 13A shows a side view of a second exemplary embodiment of the injection device during the idle stroke, FIG. 13B shows a sectional view corresponding to FIG. 13A, FIG. 15A shows a side view of the second exemplary embodiment of the injection device after completed withdrawal of the needle, FIG. 15B shows a sectional view corresponding to FIG. 15A, FIG. 17A shows a side view of the second exemplary embodiment of the injection device during resetting of the minimum retention time mechanics, FIG. 17B shows a sectional view corresponding to FIG. 17A.

DESCRIPTION OF THE EXEMPLARY EMBODIMENT

Figure 7A:
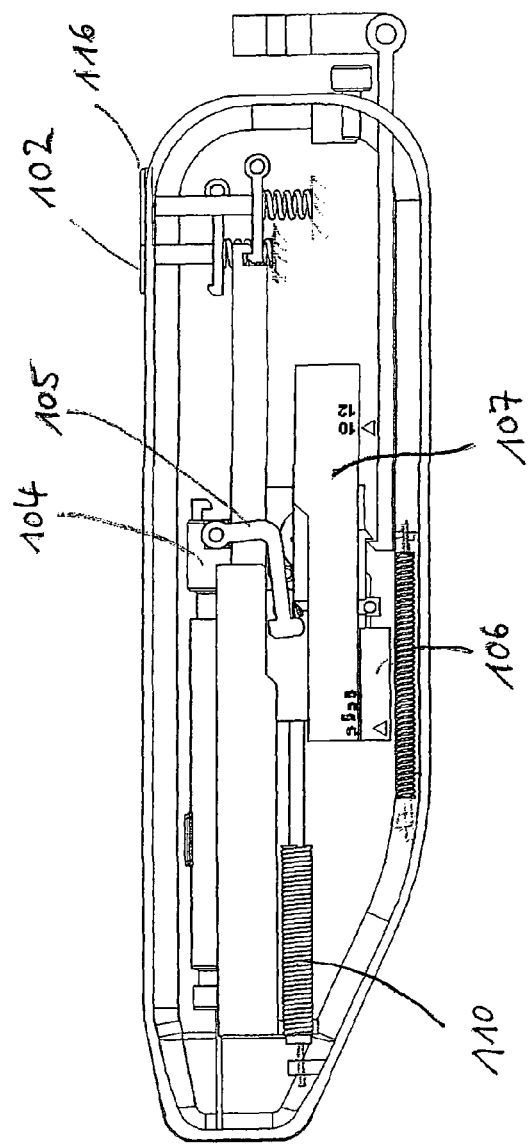
FIG. 7A shows a side view of the first exemplary embodiment of the injection device after completed withdrawal of the needle.
Figure 7B:
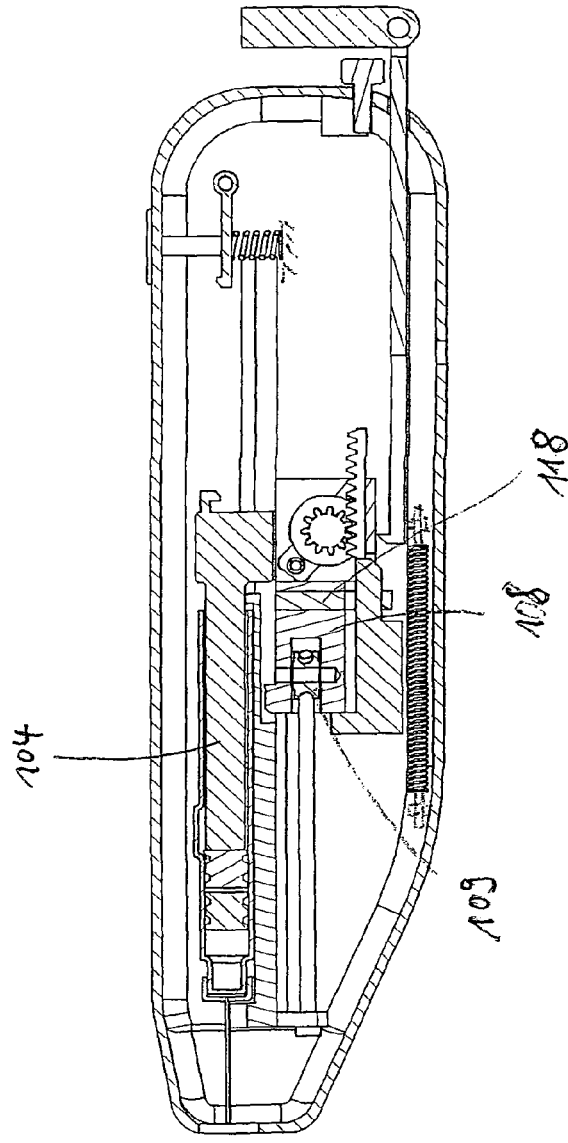
FIG. 7B shows a sectional view corresponding to FIG. 7A.

To inject the active substance, a two-chamber ampoule 111 is used. An ampoule of this type (FIG. 1B) has two pistons 111A, 111B, resulting in two initially independent chambers 111C, 111D. Into the first, inner chamber 111C, which faces the cannula 112, powdered Betaferon, for example, is filled, and into the second, outer chamber 111D, a NaCl solution is filled.

If a ram 104 is now pressed against the outer piston 111B, the inner piston 111A is initially displaced as well, as the NaCl solution hydraulically transfers the force of the ram onto the inner piston 111A. As soon as the inner piston 111A has passed an overflow channel 111E in the form of a groove-like convexity in the outer wall of the ampoule 111, it comes to a standstill and the NaCl solution flows through this overflow channel 111E into the inner chamber 111C and mixes with the Betaferon. After the mixing process, the injection then takes place (after the puncture stroke) due to the continued movement of the ram 104.

FIG. 1A shows a top view, FIG. 1B shows a sectional view in the starting position of the injection device.

All the components are situated inside a housing 101 composed of two tub-shaped half-shells. The movable components are held inside the injection device so as to be displaceable parallel to the longitudinal axis of the needle. The components are assigned to each other as follows:

A two-chamber ampoule 111 is held in a receptacle 103. A ram 104, to the rearward end of which a control lever 105 is hinged, is held on a locking hook 102A of a spring-actuated first push-button 102. The receptacle 103 is held on a locking hook 116A of a spring-actuated second push-button 116.

Acting on the receptacle 103 is the end of a traction cable 114 that is deflected via a roller 109 mounted in a carriage 108 and connected to a tension spring 110 fixed to the housing 101. The tension spring 110 accordingly exerts a pulling force on the receptacle 103 in a direction away from the injection site. The receptacle 103 cannot slide in an axial direction, however, because it is held by the locking hook 116A on the second push-button 116.

The deflection of the traction cable 114 via the roller 109 creates a force on the carriage 108 toward the injection site. The carriage 108 remains it its position, however, because it rests against the ram 104 via a driving feature 118, which is mounted in the carriage 108 so as to be displaceable perpendicular relative to the injection device and which is actuated by a driving spring 119, and the ram 104 is held by the locking hook 102A on the first push-button 102.

Assigned to the control lever 105 is a first adjusting slider 107, in which a second adjusting slider 106 is displaceably supported. The adjusting slider 106 provides for the uncoupling of the carriage 108 from the ram 104. The adjusting sliders 106, 107 are designed as displaceably supported limit-stop elements for adjustment of the needle-insertion depth and injection volume, as will be explained further below.

A pull-back handle 117, which is connected to a pull rod 115, serves to create this starting position. The pull rod 115 is actuated by a pull-back spring 120.

When the first push-button 102 is actuated, this causes the locking hook 102A to move out of engagement, the ram 104 is released and moves toward the puncture site until the front edge of the control lever 105 comes to rest against the receptacle 103. This causes the outer piston 111B of the ampoule 111 to be activated, it moves forward and carries out a mixing stroke H0. This mixing stroke serves for mixing of the NaCl solution with the Betaferon, as described above (FIG. 2A, FIG. 2B). A window in the housing 101 makes it possible to monitor the mixing of the Betaferon with the NaCl solution.

Since the free end of the control lever 105, on the other hand, slides on the second adjusting slider 107 and rests on it, it cannot yield in a downward direction by pivoting at this location; the pulling force of the tension spring 110 toward the puncture site is therefore transferred from the carriage 108 via the ram 104 to the receptacle 103. The receptacle 103 remains in its position, however, because it is locked in place by the locking hook 116A of the push-button 116.

When the second push-button 116 is now actuated, this causes the locking hook 116A to move out of engagement and the receptacle 103 is released; this causes the ram 104 and the receptacle 103 to jointly move toward the puncture site under the action of the tension spring 110. The needle is inserted (FIG. 3A, 3B), the injection stroke H1 is carried out (FIG. 4A, 4B.)

Once the desired insertion depth is reached, the control lever 105 is able to pivot downward (arrow in FIG. 4A), since it is no longer prevented from doing so by the first adjusting slider 107 because of its recessed upper surface. Consequently, force is no longer transferred from the ram 104 to the receptacle 103, the receptacle 103 remains in its position and only the ram 104 continues to move toward the injection site, i.e. injection of the medication takes place, the injection stroke H2 is carried out.

Once the driving feature 118 that is displaceably mounted in the carriage 108 reaches the ramp 106A of the second adjusting slider 106 (FIG. 4B), the driving feature 118 is pulled downward and the carriage 108 is thus uncoupled from the ram 104, i.e. at this point in time the injection is complete (FIG. 5B).

In FIG. 5, a toothed rack 140, which is mounted by means of a first adjusting screw 130 in the housing between a front and rear end position so as to be able to be freely displaced by the user, is shown in its frontal end position, in which the retention time is set to the maximum (maximum duration of the idle stroke HX).

Once the injection is complete, the toothed rack 140 strikes the second adjusting slider 106, the carriage 108 continues to move jointly with a damping element 150 that is connected to the carriage 108, relative to the toothed rack 140, toward the puncture site, thereby causing the idle stroke HX to occur, during which the needle remains in the puncture site. The relative movement between the toothed rack 140 and the damping element 150 during the idle stroke HX causes the damping element 150 to become operative. Once the carriage 108 strikes the second adjusting slider 106, the idle stroke HX is complete.

If the toothed rack 140 is not in its frontal end position it strikes the second adjusting slider 106 at a later point in time and the duration for which the damping element 150 is effective is accordingly shorter as well, as is the retention time (duration of the idle stroke HX).

If the retention time is set to the minimum value, the toothed rack 140 strikes the carriage 108 only after completion of the idle stroke HX and is not displaced relative to the carriage 108 and damping element 150; the damping element 150 has no effect and therefore does not influence the retention time.

The carriage 108 now rests against the second adjusting slider 106. Since the second adjusting slider 106 is held form-fittingly on the housing 101 via the first adjusting slider 107, the pulling force of the tension spring 110 (which is fixed to the housing 101) now acts via the roller 109 on the receptacle 103, causing the same to be pulled back and consequently causing the needle to be pulled out of the puncture site (FIG. 6A, 6B), the retraction stroke H3 is carried out.

Figure 8A:
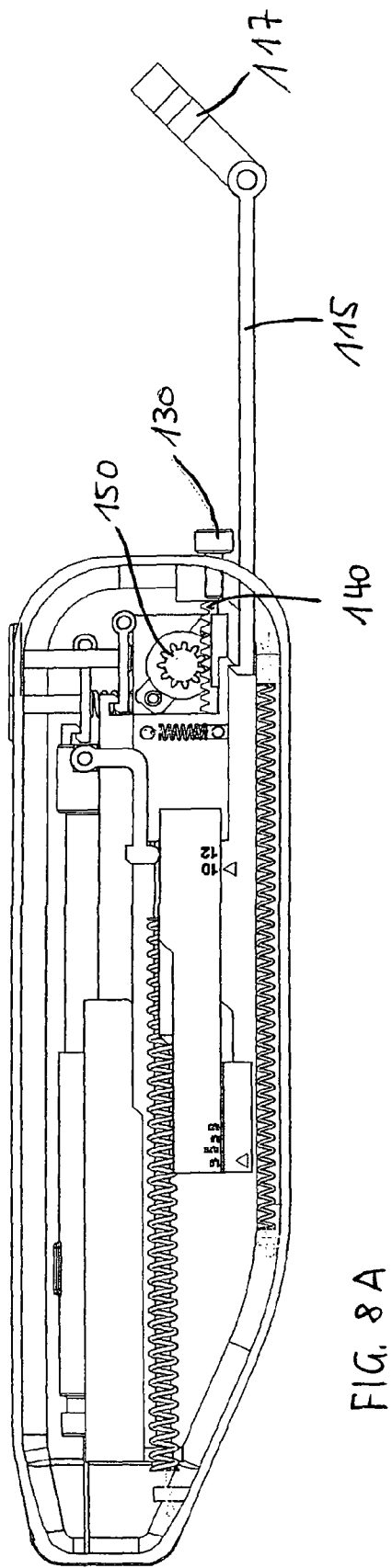
FIG. 8A shows a side view of a first exemplary embodiment of the injection device during resetting of the mechanics (maximum retention time)
Figure 8B:
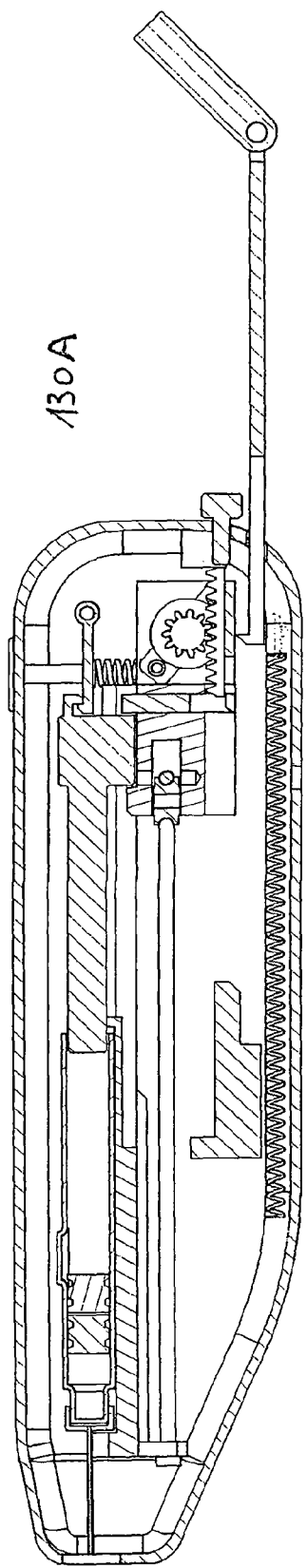
FIG. 8B shows a sectional view corresponding to FIG. 8A.

By folding down the pull-back handle 117, which is connected to the pull rod 115, and by pulling out the pull rod 115, the carriage 108 and all other elements are pulled back into their starting position (FIG. 8A, 8B).

During the process of pulling back the carriage/damping element into the starting position, the toothed rack 140 strikes the frontal first limit-stop surface 130A of the adjusting screw 130. While the carriage 108 with the damping element 150 continue to move away from the puncture site the toothed rack 140 is held in position by the adjusting screw 130, i.e. the toothed rack 140 moves, relative to the carriage 108/damping element 150, into the selected starting position.

The position of the surface 130A can be changed by means of the adjusting screw, and thereby the distance by which the toothed rack 140 is displaced relative to the carriage 108/damping element 150.

Figure 9A:
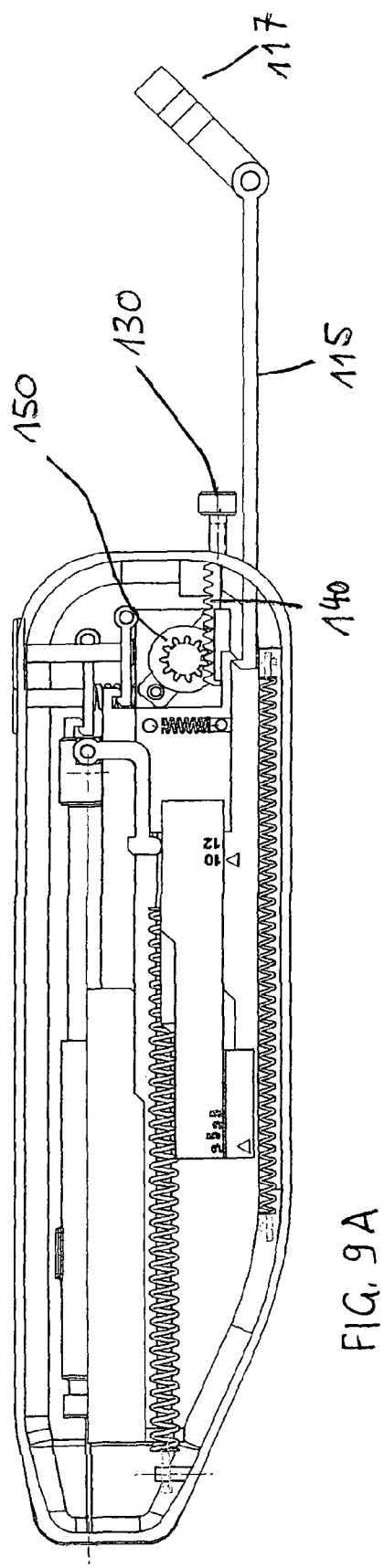
FIG. 9A shows a side view of a first exemplary embodiment of the injection device during resetting of the mechanics (minimum retention time)
Figure 9B:
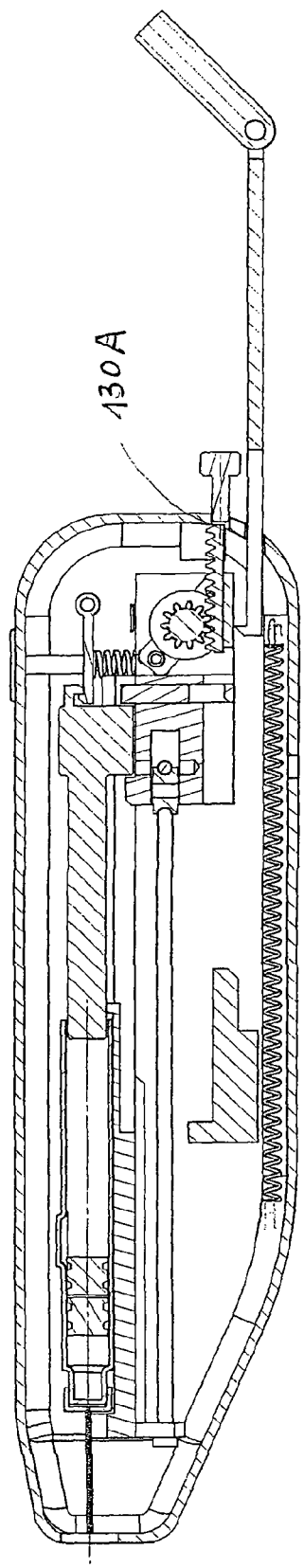
FIG. 9B shows a sectional view corresponding to FIG. 9A.
Figures 10A, 10B:
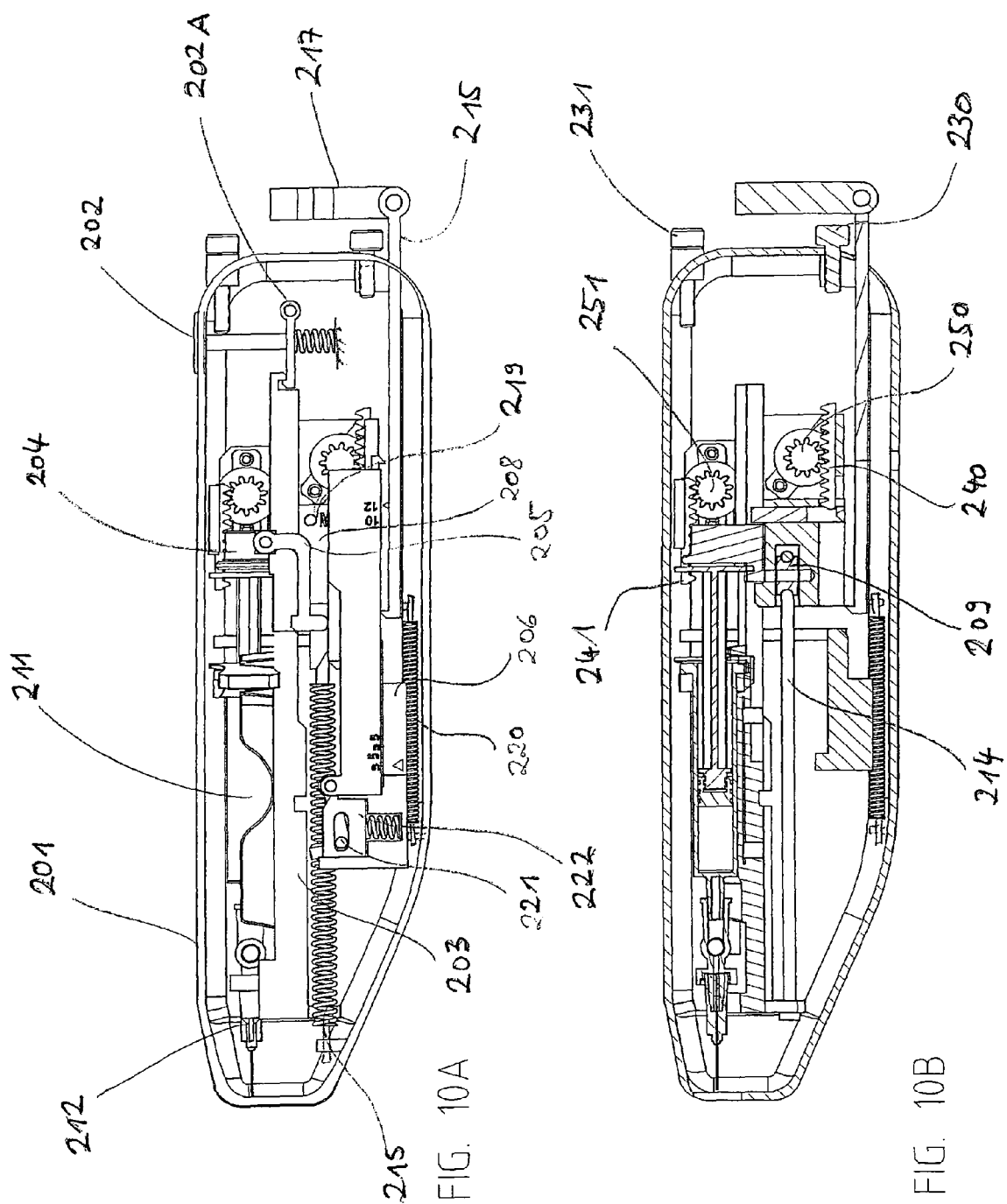
FIG. 10A shows a side view of a second exemplary embodiment of the injection device with the housing cover removed.
FIG. 10B shows a section through the injection device of FIG. 1 in its starting position in its center plane 1.

FIG. 8A/8B shows the adjusting screw 130 in the position that produces the maximum retention time. FIG. 9A/9B shows the adjusting screw in the position that produces the minimum retention time. Between these two positions the retention time may be adjusted continuously.

Once the mechanism has been moved back into the starting position, the carpule can now be removed.

The injection volume and needle insertion depth can be adjusted as follows:

The first adjusting slider 107 is mounted in the housing 101 so as to be axially displaceable, in the present example with 2 locking positions (10 and 12 mm, set to 10 mm in the example). These locking positions are assigned to the puncture stroke H1, since the axial position of the adjusting lever 107 determines the distance traveled until the control lever 105 uncouples the ram 104 from the receptacle 103 (FIG. 2A).

Mounted inside the first adjusting slider 107 in a manner so as to also be axially displaceable is the second adjusting slider, in the present example with 4 locking positions (1.0; 0.75; 0.5; 0.25; in the example set to 1.0 mm). These locking positions are assigned to the injection stroke H2, since the axial position of the adjusting slider 106 determines the distance traveled until the ram 104 is uncoupled from the carriage 108 (FIGS. 5A,5B) and withdrawal of the needle takes place.

If a needle insertion depth of 12 mm, for example, is now to be set, the first adjusting slider 107 must be displaced by 2 mm toward the puncture site, relative to the depicted state, to the new locking position on the housing 101. Since the second adjusting slider 106 is interlocked in position 1.0 with the first adjusting slider 107, the same now also moves by 2 mm toward the puncture site, i.e. setting a different needle insertion depth has no impact on the injection volume setting. Likewise, adjusting the injection volume has no impact on the needle insertion depth; the settings of the puncture stroke H1 and injection stroke H2 are independent from each other.

The second exemplary embodiment shown in FIGS. 10-17 proceeds from an injection device as described in the first exemplary embodiment, however, not for use with a carpule but with a hypodermic syringe, i.e. a mixing stroke does not take place. The basic concept of this exemplary embodiment is that the injection duration and/or retention time can be set by the patient.

The design and interaction of the components explained in connection with the first exemplary embodiment are identical in their functions, so that only the additional components will be described below based on their functions:

Setting the Duration of the Injection Stroke:

Upon actuation of the first push button 202, the locking hook 202A moves out of engagement and the receptacle 203 is released; this causes the ram 204 and the receptacle 203 to jointly move toward the puncture site under the action of the tension spring 210. The needle is inserted (FIGS. 11A and 11B), the puncture stroke is carried out.

Upon completion of the puncture stroke a locking mechanism 221, which is subjected via a slotted hole inside a guide means 222 to a force acting in the direction of the receptacle (triggered by a spring 223), is able to pivot into the recess in the receptacle 203. This locking mechanism is supported in the first adjusting slider 207 and is therefore independent from the selected needle insertion depth. The receptacle 203 is fixed in the inserted position via the locking mechanism 221.

Once the desired insertion depth is reached, the control lever 205 is able to pivot downward (arrow in FIG. 12A), since it is no longer prevented from doing so by the first adjusting slider 207 because of its recessed upper surface.

Consequently, force is no longer transferred to the ram 204.

FIG. 11A shows the state of the injection device at the maximum injection duration setting, i.e. a toothed rack 241 makes contact simultaneously with the end of the puncture stroke with a limit stop 206B of the second adjusting slider 206.

If the injection duration is set to a smaller value, the toothed rack 241 strikes the limit stop 206A at a later point in time.

After the ram 204 is uncoupled from the receptacle 203, the receptacle 203 remains in its position and the ram 204 continues to move toward the puncture site. Starting from the point in time at which the toothed rack 241 strikes the limit stop 206B of the second adjusting slider 206, the same remains stationary relative to the ram 204 and to a damping element 251 and the injection stroke is accordingly slowed by the damping element 251. The injection duration is therefore dependent upon the distance along which the damping element 251 is effective, and this distance is adjustable by the patient by means of an adjusting screw 231. Injection of the medication takes place, the injection stroke is carried out.

Once the driving feature 218 that is displaceably supported in the carriage 108 reaches the ramp 206A of the adjusting slider 206 (FIG. 12b), the driving feature 118 is pulled downward and the carriage 208 is accordingly uncoupled from the ram 204, i.e. at this point in time the injection is complete (FIG. 13b).

Setting the Retention Time:

In FIG. 13B the toothed rack 240 is shown in its frontmost position, i.e. the retention time is set for the maximum. Once the injection is complete the toothed rack 240 strikes the second adjusting slider 206, the carriage 208 continues to jointly move with the damping element 250 relative to the toothed rack 240 toward the insertion site. The relative movement between the toothed rack 240 and damping element 250 during the idle stroke HX causes the damping element 250 to take effect. Once the carriage 208 strikes the second adjusting slider 206, the idle stroke HX is complete.

If the toothed rack 240 is not in its frontmost position (shorter retention time) it strikes the second adjusting slider 206 at a later point in time and the distance along which the damping element 250 is effective is accordingly smaller, and so is the retention time.

If the retention time is set to the minimum value, the toothed rack 240 strikes the carriage 208 only after completion of the idle stroke HX and is not displaced relative to the carriage 208 and damping element 250, the damping element 250 has no effect and does not influence the retention time.

Figure 14A:
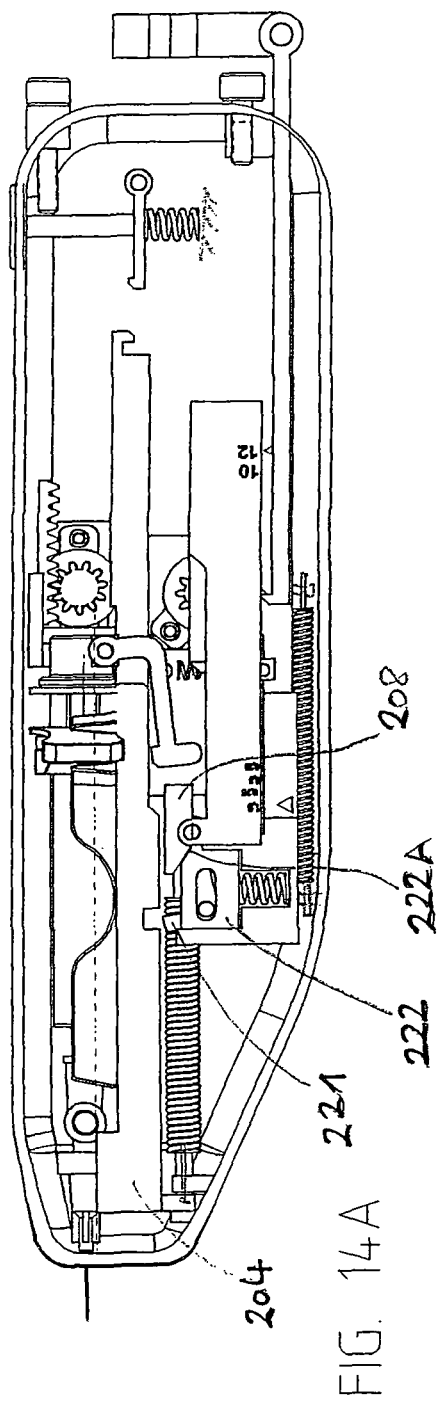
FIG. 14A shows a side view of the second exemplary embodiment of the injection device during withdrawal of the needle.
Figure 14B:
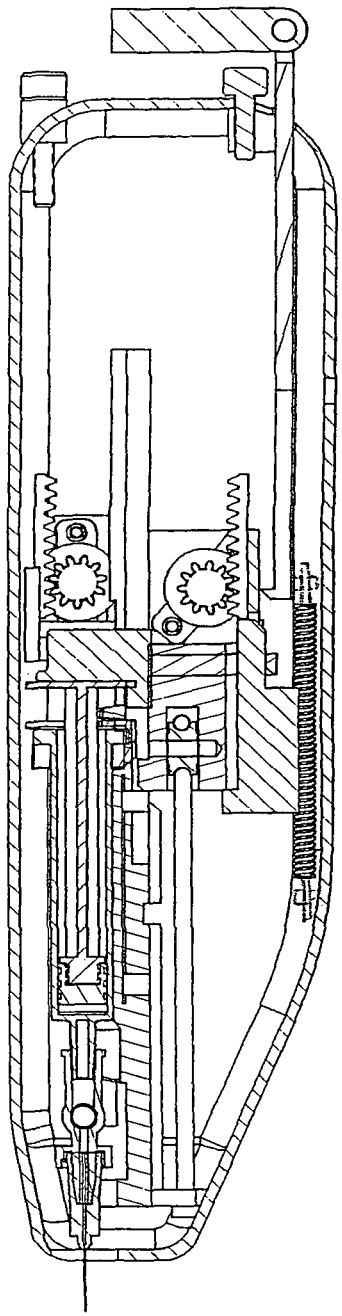
FIG. 14B shows a sectional view corresponding to FIG. 14A.

At the end of the idle stroke, the incline of the carriage 208 strikes a ramp 222A of a guide means 222 and releases the locking mechanism between the receptacle 203 and adjusting slider 206 (FIG. 14A).

The carriage 208 now rests against the second adjusting slider 206. Since the second adjusting slider 206 is held form-fittingly on the housing 201 via the first adjusting slider 207, the tension spring 210 (which is fixed to the housing 201) now acts via the roller 209 on the receptacle 203, causing the same to be pulled back and thus pulls the needle out of the puncture site (FIG. 15A,15B), the retraction stroke H3 is carried out.

Figure 16A:
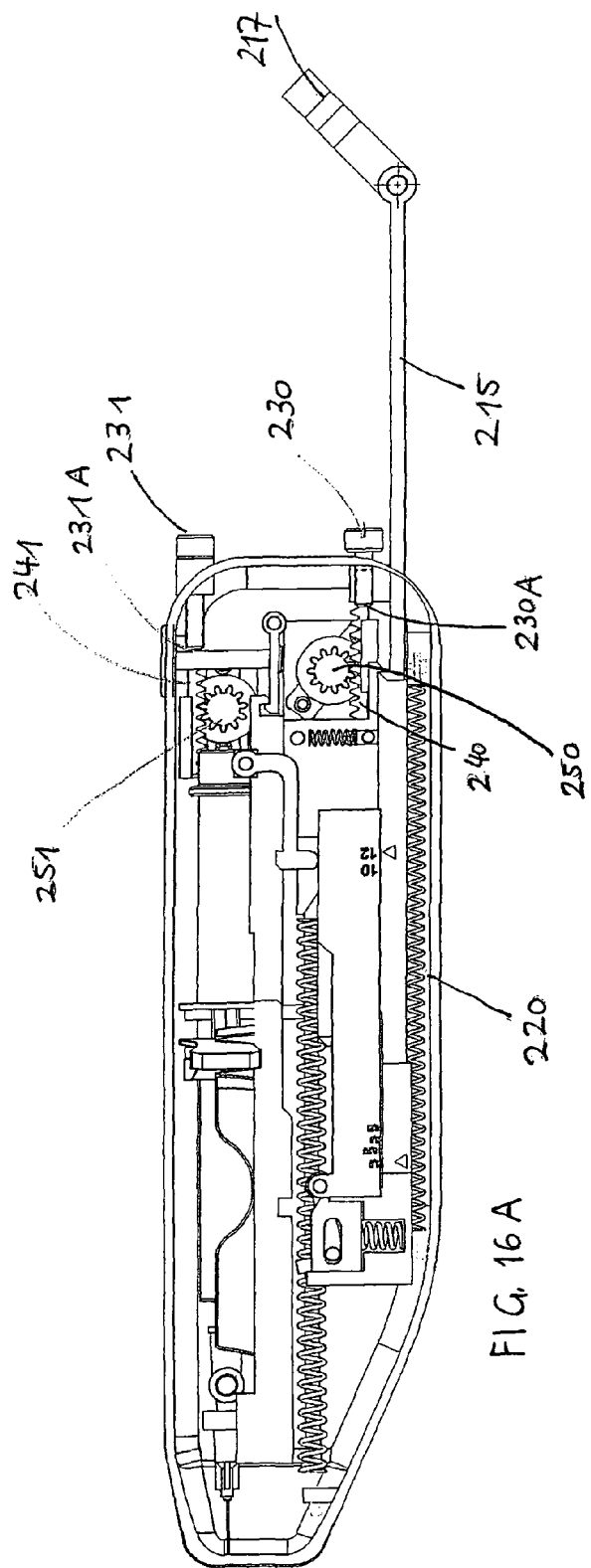
FIG. 16A shows a side view of the second exemplary embodiment of the injection device during resetting of the maximum retention time mechanics.
Figure 16B:
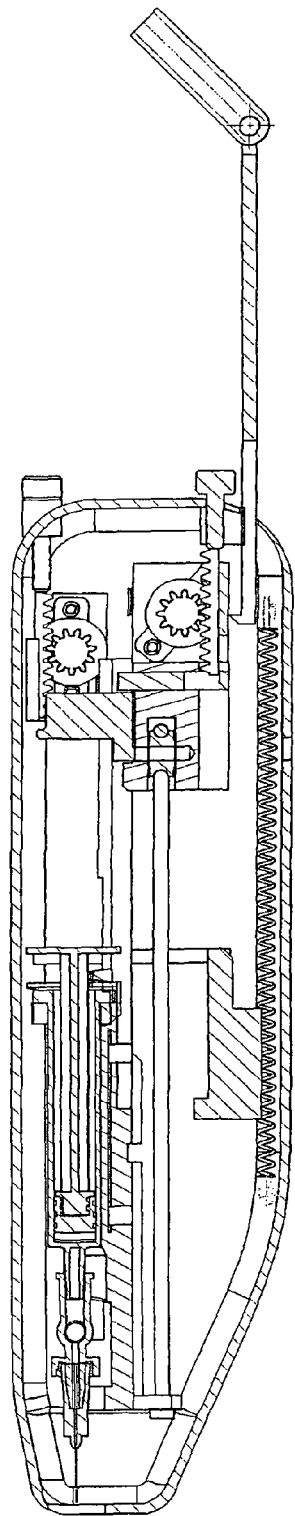
FIG. 16B shows a sectional view corresponding to FIG. 16A.

By folding down the pull-back handle 217 that is connected to the pull rod 215, and pulling out the pull rod 215, the carriage 208 and all other elements are pulled back into the starting position (FIGS. 16A, 16B).

During the process of pulling back the carriage 208/damping element 250 and ram 204/damping element 251 into the starting position, the toothed rack 240 strikes the surface 230A of the adjusting screw 230, and the toothed rack 251 strikes the surface 231A of the adjusting screw 231. While the carriage 208/damping element 250 or ram 204/damping element 251 continue to move away from the puncture site the toothed rack 240 is held in position by the adjusting screw 230 and the toothed rack by the adjusting screw 231, i.e. the toothed racks 240/241 move relative to the damping elements 250/251 into the selected starting position.

The position of the limit-stop surfaces 230A/231 can be changed by means of the adjusting screws 230/231. The distances by which the toothed racks 240/241 move relative to the damping elements 250/251 is adjustable by the patient.

FIGS. 16A/16B show the adjusting screws 230 and 231 in the position that produces the maximum retention time/injection duration.

FIGS. 17A/17B show the adjusting screws 230 and 231 in the position that produces the minimum retention time/injection duration. Between these two positions, the retention time (duration of the idle stroke HX) and injection duration (duration of the injection stroke H2) may be adjusted continuously, independently from each other.

After the mechanism has been moved back into the starting position, the syringe 211 can now be removed.

In the described exemplary embodiments it is accordingly possible for the user, so as to adjust the duration of the injection stroke by means of an appropriate design of the damping element, to adjust the duration of the effect of the damping element within a stroke by displacing the associated toothed rack, so that a portion of the stroke proceeds undamped, the remaining portion damped.

Alternatively, a damping element may be used whose damping characteristics can be adjusted by the user to thereby vary the duration of the stroke.

Combinations of such measures for generating a desired process characteristic (speed profile) of a stroke are possible as well.

To implement these alternatives for a user-defined adjustment of the speed/duration of a stroke, for instance of the injection stroke, a rotation damping element of a commercially available type may be used in the described exemplary embodiments.

Advantageously, a rotation damping element may be used, such as the one described in DE 20 2006 017 578.3 U1. With the latter, it is possible to set a basic damping, permitting an even more flexible adaptation of the progression profile of a stroke to the individual requirements of a user.

If the desired variation of the duration of the respective stroke is already attainable via the adjusting range of this basic damping provided by a rotation damping element according to DE 20 2006 017 578.3 U1, the adjustment of the associated toothed rack by means of its associated adjusting screw may be dispensed with, if appropriate, and the same may then remain in the position in which it permits the maximum stroke duration.

Figure 18:
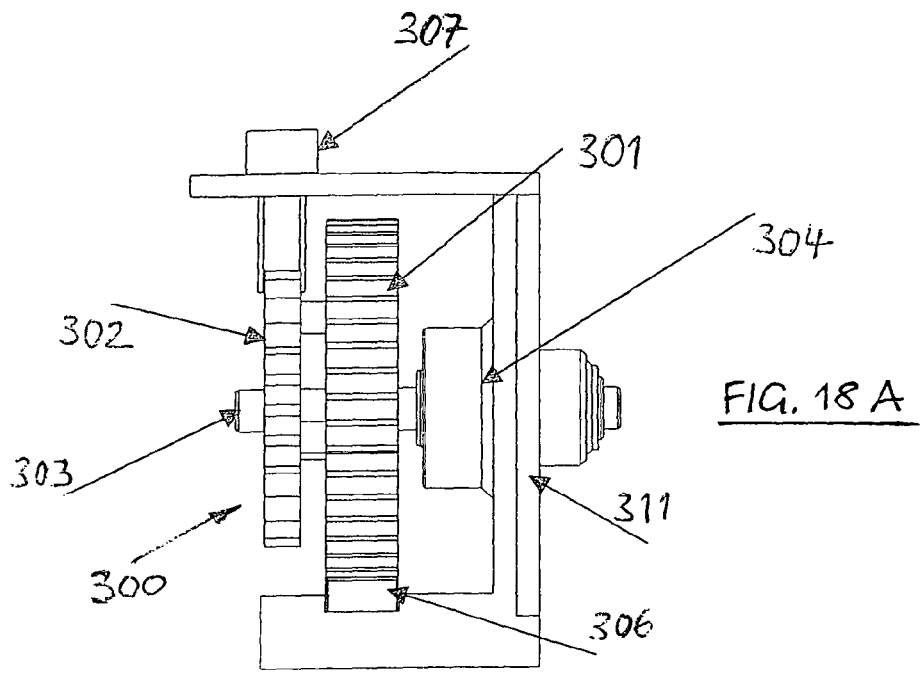
FIG. 18A shows a side view of a first exemplary embodiment of a planetary gear with a rotation damping element.
FIG. 18B shows a sectional view corresponding to FIG. 18A.
FIG. 18C shows a sectional view of the planetary gear without planetary carrier
FIG. 18D shows a perspective view corresponding to FIG. 18A with blocked planetary carrier.
FIG. 18E shows a perspective view corresponding to FIG. 18C without planetary carrier.
FIG. 18F shows a view corresponding to FIG. 18D with blocked planetary carrier.
Figure 18:
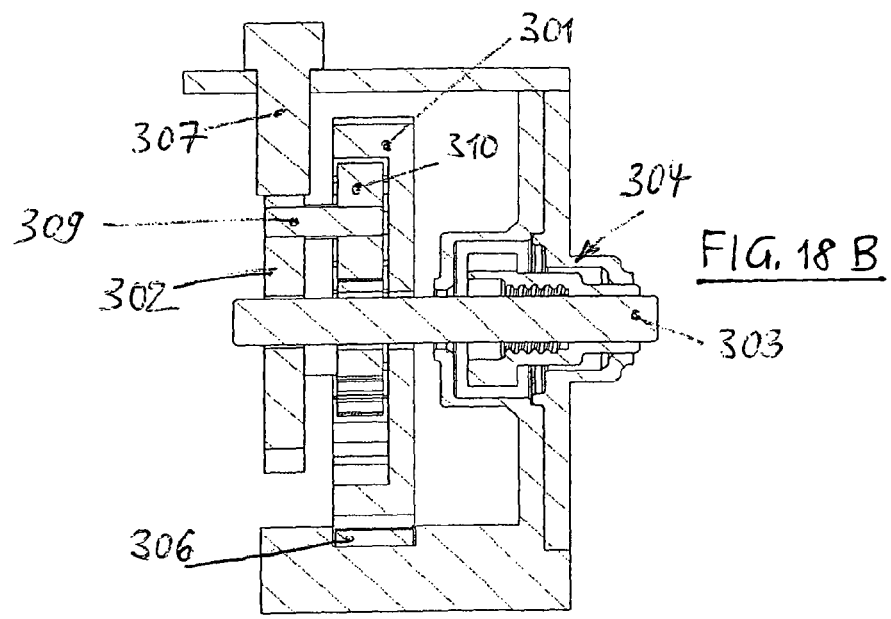
Figure 18:
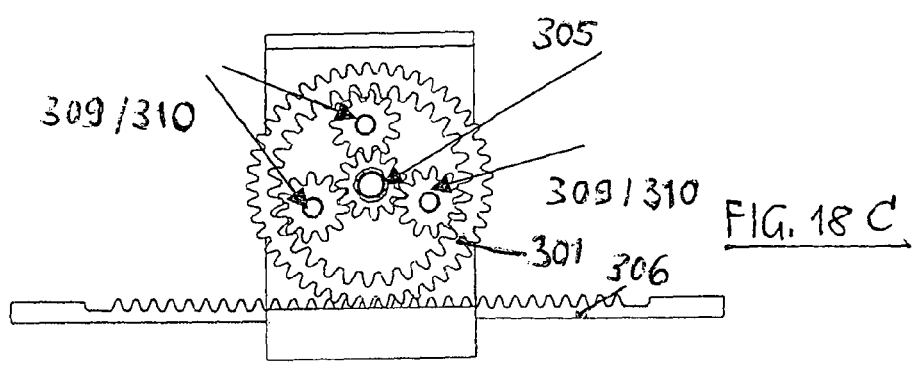
Figure 18:
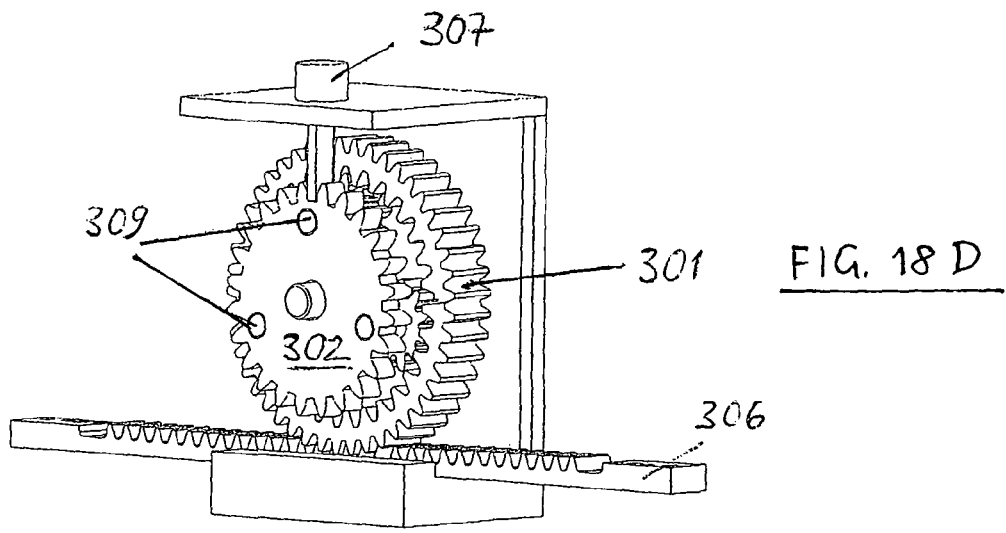
Figure 18:
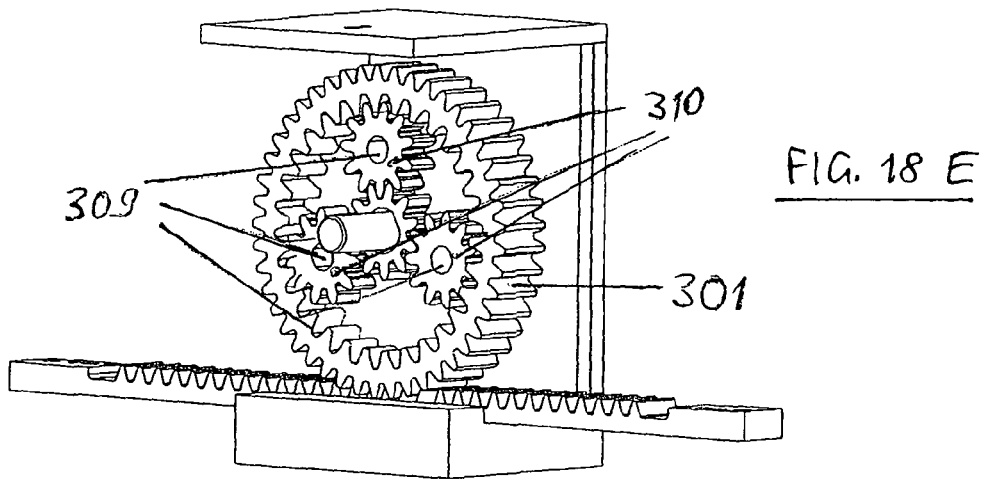
Figure 18:
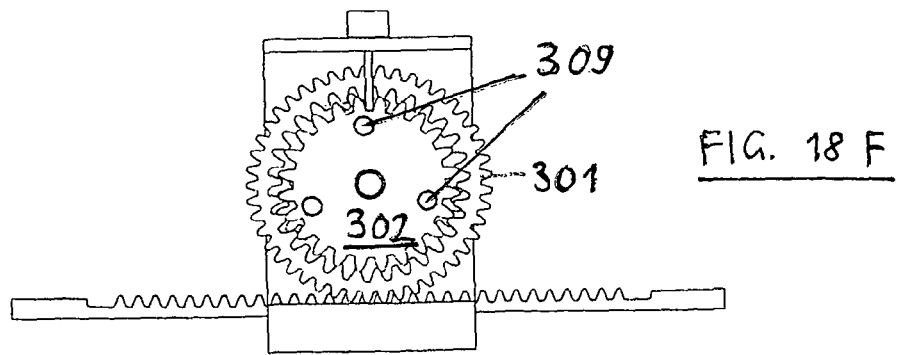
Figure 19:
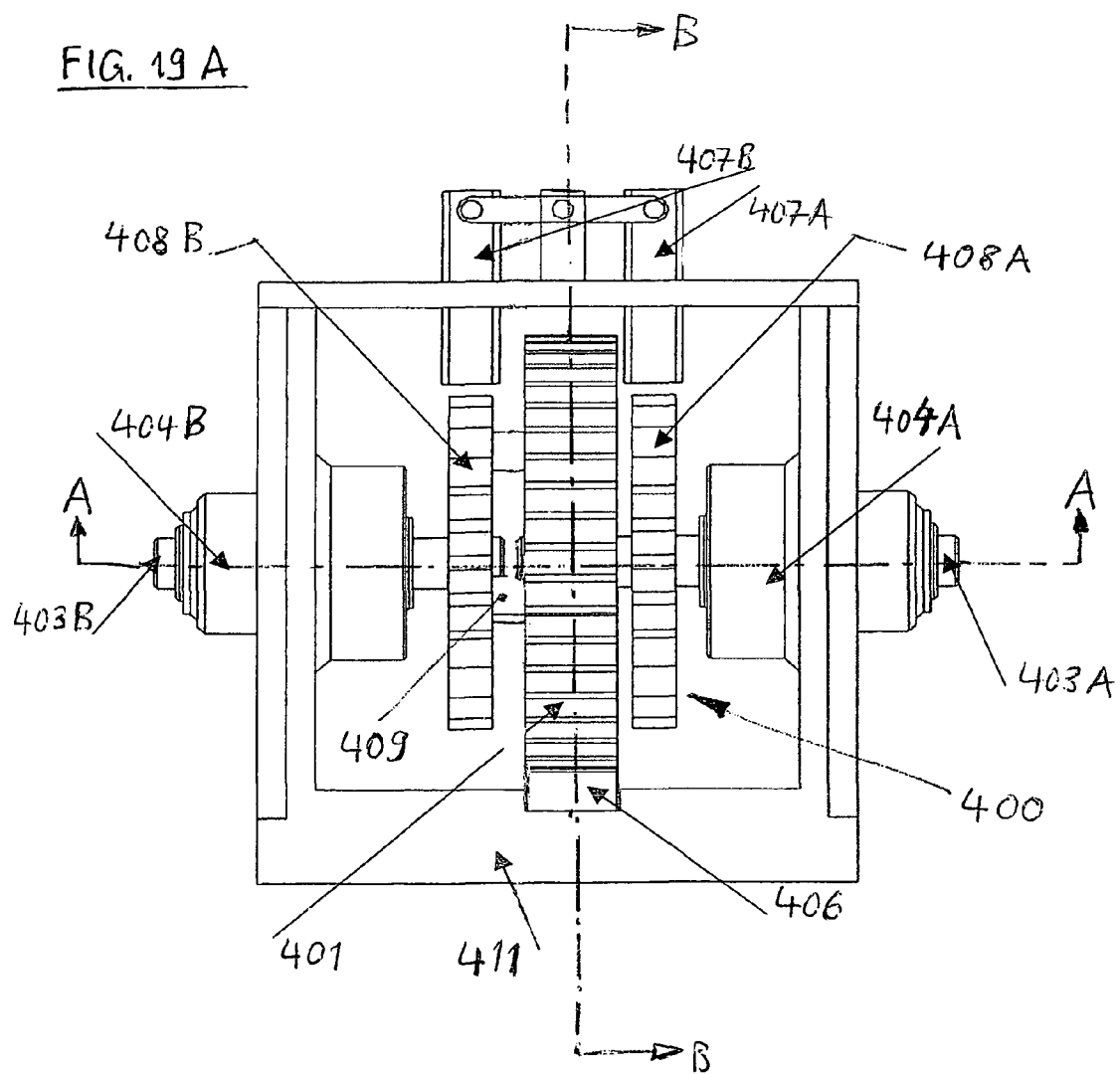
FIG. 19A shows a side view of a second exemplary embodiment of a planetary gear with two rotation damping elements.
FIG. 19B shows a side view and a perspective view according to FIG. 19A with a locked first blocking disk.
FIG. 19C shows a side view and a perspective view corresponding to FIG. 19B with a locked second blocking disk.
FIG. 19D shows a perspective view corresponding to FIG. 19B with a locked first blocking disk, FIG. 19E a perspective view corresponding to FIG. 19D without planetary carrier/second blocking disk.
FIG. 19F shows a section in the plane B-B of FIG. 19A.
FIG. 19G shows a first section in the plane A-A of FIG. 19A.
FIG. 19H shows a second section in the plane A-A of FIG. 19A.
Figure 19:
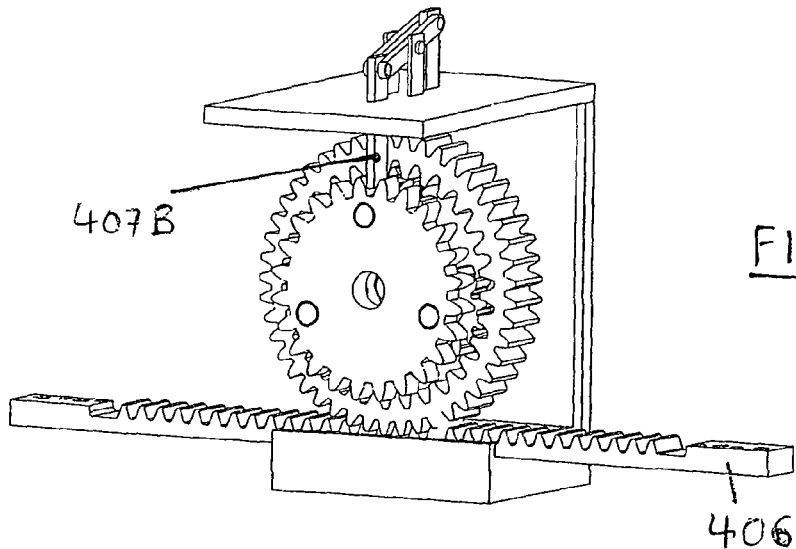
Figure 19:
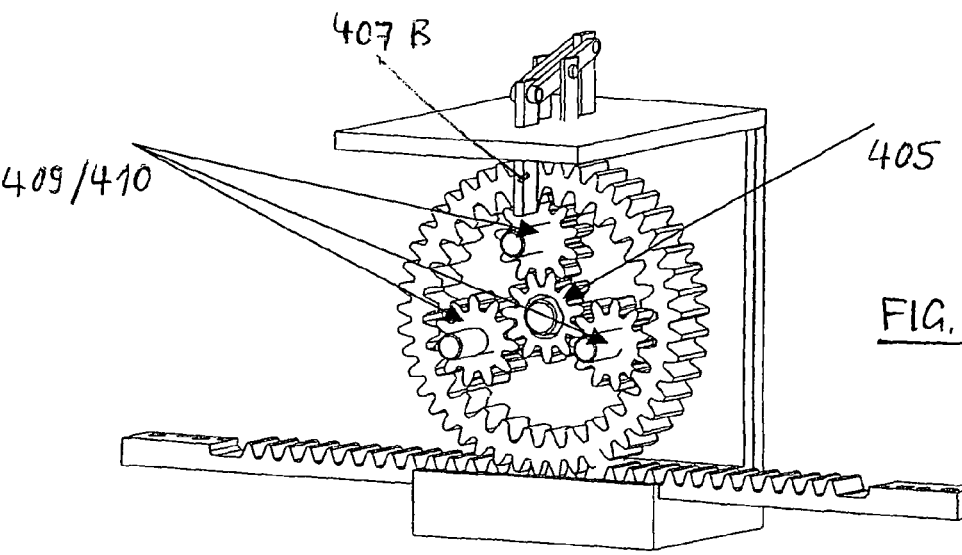
Figure 19:
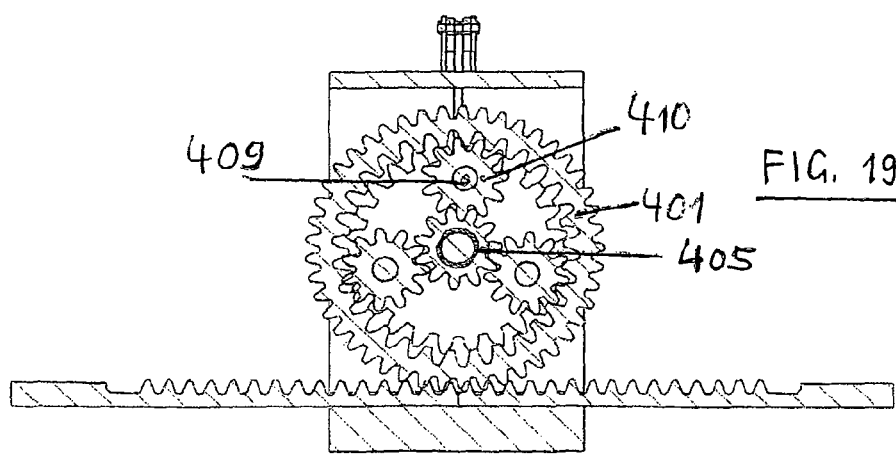
Figure 19G:
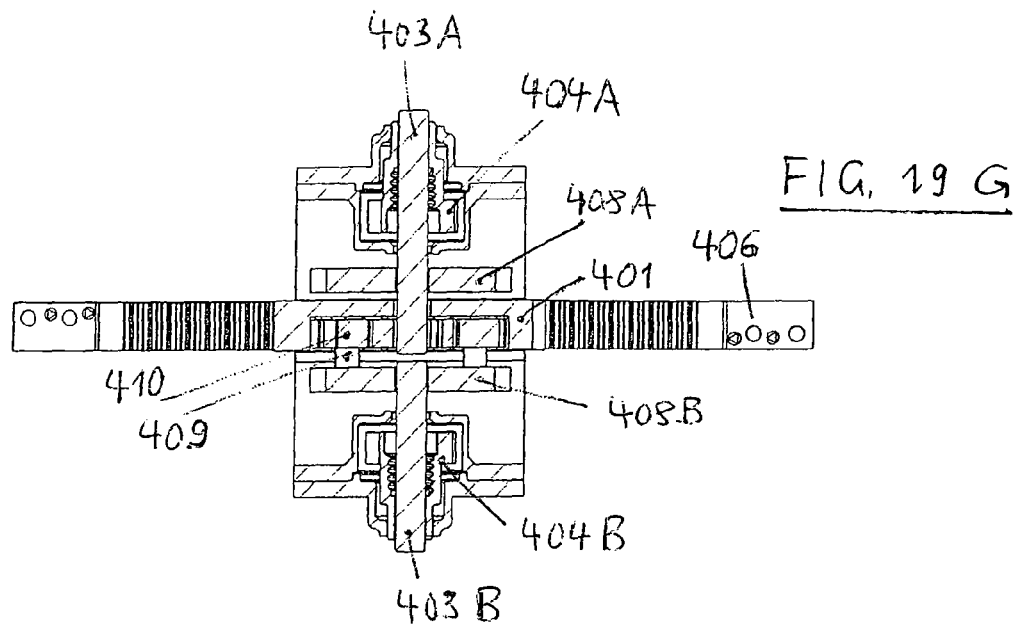
Figure 19H:
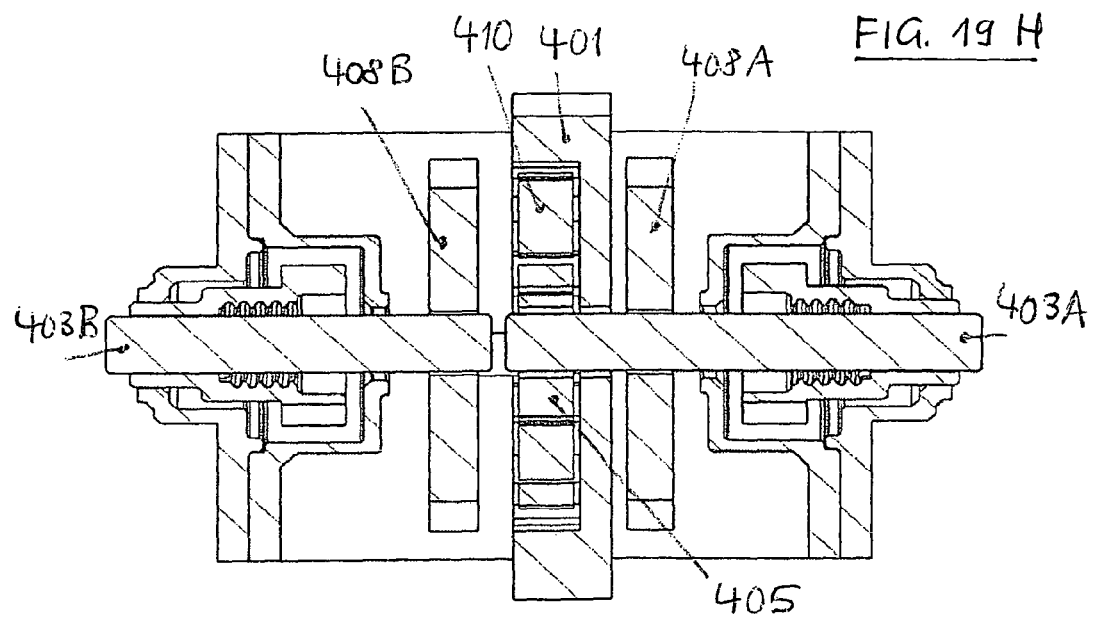

FIGS. 18 and 19 show two exemplary embodiments of a damping element in which the coupling of the toothed rack, as the stroke-determining component, to one/two rotation damping element(s) is effected by means of a planetary gear that is designed, by means of a locking element, as an On/Off switch for the rotation damping element. The components are supported and/or held in a housing 311,411.

The first exemplary embodiment shown in FIGS. 18A-18F is designed as follows:

The annulus gear 301 and the planetary carrier 302 of a planetary gear 300 are supported freely rotating on the shaft 303. The sun gear 305 is rigidly press-fitted to the shaft 303 and thus acts as a drive for the rotation damping element 304 connected to the shaft 303.

The planetary carrier 302 is rigidly connected via three axes 309 to the three planet gears 310. They rotate about the sun gear 305 via a toothing. The annulus gear 301 is driven via the toothed rack 306. A blocking slide 307 is able to prevent the planetary carrier 302 from turning by engaging into its toothing. Depending on the position of the blocking slide 307, the respective gears are operated in the following modes:

The planetary carrier 302 is not blocked (FIGS. 18C,E):

The blocking slide 307 is not blocking the planetary carrier 302. The annulus gear 301 rotates, causing the planet gears 310 to rotate about the sun gear 305, thereby effecting a rotation of the planetary carrier 302. The sun gear 305, accordingly, is not moving and the rotation damping element 304 is therefore not driven. This means that an idle movement takes place, i.e. the stroke of the injection device that is coupled to the toothed rack 306 proceeds undamped with maximum speed and therefore in the shortest amount of time.

The planetary carrier 302 is blocked (FIGS. 18A,B,D,F):

The blocking slide 307 engages into the planetary carrier 302. The annulus gear 301 rotates because of the linear movement of the toothed rack 306. The annulus gear 301 drives the planet gears 310. Since the planetary carrier 302 is fixed in its position, the individual planet gears 310 cannot rotate about the sun gear 305. The planet gears 310 accordingly drive the sun gear 305. Since the same is connected via the shaft 303 to the rotation damping element 304, the same is being driven. This means that a damping takes place, i.e. the stroke of the injection device that is coupled to the toothed rack 306 proceeds at a reduced speed/over a longer duration.

If two rotation damping elements with different damping values that are placed in series are operated in this manner, a plurality of combinations are possible:

1) None of the two blocking slides is depressed→idle movement, no stroke damping,
2) only one blocking slide is depressed→only the associated rotation damping element is damping, stroke damping based on the selected rotation damping element,
3) both blocking slides are depressed→both rotation damping elements are damping, maximum damping of the stroke.

The second example shown in FIGS. 19A-19H expands upon the first example and is designed as follows:

Two shafts 403A and 403B are provided. The first shaft 403A serves as a drive for the first rotation damping element 404A. Rigidly disposed on, e.g. pressed onto the first shaft 403A is a first blocking disk 408A. The annulus gear 301 rotates freely on the first shaft 403A. Additionally, the sun gear 405 is rigidly connected to the first shaft 403A. The drive is effected via the toothed rack 406, which drives the annulus gear 401.

The second shaft 403B serves as a drive for the second rotation damping element 404B. Rigidly disposed on the second shaft 403B is a second blocking disk 408B. The second blocking disk 408B serves as the planetary carrier, since the three planet gears 410 are connected freely rotating via the three axes 409. The planet gears 410 are driven via the annulus gear 401 and drive the respective gears in dependence upon the position of the blocking slides 407A,407B of the blocking device.

The following functions are thus created:

The first blocking disk 408 is blocked (FIG. 19C):

The blocking device blocks, via its first blocking slide 407A, the rotation of the first blocking disk 408A and thereby the rotation of the first shaft 403A. The annulus gear 401 rotates, due to the linear movement of the toothed rack 406, and drives the planet gears 410.

Since the first shaft 403A cannot rotate, the sun gear 405 is fixed in its position. The planet gears 410 can therefore move about the sun gear 405, thereby driving the planetary carrier/second blocking disk 408B. Since the same is connected via the second shaft 403B to the second rotation damping element 404B, the second rotation damping element 404B is being driven. A damping therefore takes place via the second rotation damping element 404B. (The second blocking disk 408B rotates without effect.)

The second blocking disk 408B is blocked (FIGS. 19B,D, E):

The blocking device blocks, via its second blocking slide 407B, the rotation of the second blocking disk 408B and accordingly the rotation of the second shaft 403B. The annulus wheel 401 rotates due to the linear movement of the toothed rack 406 and drives the planet gears 410. Since the planet carrier (=second blocking disk 408B) is fixed in its position, the planet gears 410 cannot move about the sun gear 405. The planet gears 410 accordingly drive the sun gear 405. Since the same is connected via the first shaft 403A to the first rotation damping element 404A, the same is being driven. A damping of the stroke accordingly takes place via the first rotation damping element 404A. (The first blocking disk 408A rotates without effect.)

The components described under FIGS. 17 and 18 with the designations "toothed rack 306,406/planetary gear set 300, 400/rotation damping element 304,404A,404B" may be used in the two exemplary embodiments of the injection device depicted in FIGS. 1 through 16 in lieu of the component with the designations "toothed rack 140,240,241/damping element 150,250,251" that is shown there.

By connecting the blocking slides to actuation means outside the housing in a suitable manner, a damping element can be activated or selected by the user, so as to, for example, achieve a slower injection stroke.

The patient is thereby given an added adjusting option for individually designing the progression profiles of the strokes of "his" injection device.

REFERENCE NUMERALS housing 101,201
first push-button 102,202
locking hook 102A,202A
receptacle 103,203
ram 104,204
control lever 105,205
first adjusting slider 107,207
second adjusting slider 106,206
ramp 106A,206A
limit stop 206B
carriage 108,208
roller 109,209
spring 110,210
carpule 111
syringe 211
hypodermic cannula 112,212
traction cable 114,214
pull rod 115,215
second push-button 116
locking hook 116A
pull-back handle 117,217
driving feature 118,218
driving spring 119,219
pull-back spring 120,220
blocking mechanism for receptacle 221
guide means for blocking mechanism 222
ramp 222A
spring 223
first adjusting screw 130,230
second adjusting screw 231
first limit-stop surface 130A,230A
second limit-stop surface 231A
first toothed rack 140,240
second toothed rack 241
first damping element 150,250
second damping element 251
planetary gear 300,400
annulus gear 301,401
planetary carrier 302,402
shaft 303,403A,403B
rotation damping element 304,404A,404B
sun gear 305,405
toothed rack 306,406
blocking slide 307,407A,407B
blocking discs 408A,408B
axes 309,409
planetary gears 310,410
housing 311,411

What is claimed is:

1. An injection device for accommodation and activation of a carpule or hypodermic syringe with an injection needle, and incorporating components whose relative movement effects the sequence of injection of an active substance, for which purpose a receptacle, into which the carpule or syringe is insertable and in which it is fixable, is supported inside a housing, and the receptacle is displaceable by means of a carriage, and mounted in the receptacle in a manner so as to be displaceable is a ram, which actuates one or more pistons of the carpule or syringe, and wherein a traction cable is provided for carrying out a puncture stroke, an injection stroke and a retraction stroke, the traction cable being deflected by means of a roller that is mounted on the carriage, one end of the carriage being connected to the receptacle and the other end of the carriage being connected to a tension spring, the tension spring being supported on the housing, wherein automatically and/or manually activated devices between the housing, the receptacle, the ram and the carriage control their alternating coupling to the traction cable and thereby the progression of the puncture stroke, the injection stroke and the retraction stroke, wherein the automatically and/or manually activated devices include at least one means having an adjustable position for adjustment of a progression profile of at least one of the strokes by a user.

2. An injection device according to claim 1, wherein the traction cable pulls the receptacle with the carpule or syringe and pulls the injection needle out of a puncture site via the carriage and the roller during the retraction stroke following the injection stroke, wherein the at least one means for adjustment comprise at least one first adjustment means for adjusting at the housing the duration of a movement-free state of the carpule or syringe between the injection stroke and the retraction stroke, during which the injection needle remains in the puncture site.

3. An injection device according to claim 2, wherein the first and/or a second means for adjustment includes a displaceably supported toothed rack.

4. An injection device according to claim 3, wherein the duration of an effect of a damping element is adjustable at the housing via a portion of an associated stroke by means of positioners that effect the displacement of the associated toothed rack between two end positions.

5. An injection device according to claim 4, wherein the damping element has a damping characteristic that is adjustable at the housing.

6. An injection device according to claim 2, wherein the first and/or a second means for adjustment includes at least one damping element that is actuatable from an associated toothed rack.

7. An injection device according to claim 6, wherein the at least one damping element is a rotation damping element having a gear wheel on a shaft that is acted upon by the toothed rack.

8. An injection device according to claim 7, wherein there is disposed between the rotation damping element and its toothed rack a gear mechanism.

9. An injection device according to claim 8, wherein the gear mechanism is a planetary gear, whose sun gear is rigidly connected to the shaft of the rotation damping element, whose annulus gear, which is freely rotatable on the shaft and in which planetary gears revolve, intermeshes with the toothed rack, and whose planetary carrier, which freely rotates on the shaft, can be put into engagement with a user-activated blocking slide, wherein the blocking slide prevents rotation of the planetary carrier.

10. An injection device according to claim 8, wherein two rotation damping elements are held on shafts that are disposed concentrically to each other, wherein the first shaft is rigidly connected to a first blocking disk and to a sun gear, and an annulus gear freely rotates about this first shaft, wherein the second shaft is rigidly connected to a planetary carrier that is designed so as to form a second blocking disk, and that a user-adjustable blocking element can alternatively block the rotation of one of the two blocking discs.

11. An injection device according to claim 1, wherein devices are provided for coupling the ram to the receptacle, which couple the ram to the receptacle for carrying out the puncture stroke and uncouple it for carrying out the injection stroke, wherein the at least one means for adjustment comprise at least one adjustment means for adjusting the duration between the beginning and end of the movement of the ram in the receptacle and thereby the duration of the injection stroke.

12. An injection device according to claim 1 for accommodation and activation of a carpule, wherein the puncture stroke is preceded by a mixing stroke.

* * * * *